(12) United States Patent
Ramos de la Peña

(10) Patent No.: US 8,551,114 B2
(45) Date of Patent: Oct. 8, 2013

(54) ROBOTIC SURGICAL DEVICE

(75) Inventor: Alejandro Ramos de la Peña, San Pedro Garza Garcia (MX)

(73) Assignee: Human Robotics S.A. de C.V., Nuevo Leon (MX)

( * ) Notice: Subject to any disclaimer, the term of this patent is extended or adjusted under 35 U.S.C. 154(b) by 1975 days.

(21) Appl. No.: 11/593,011

(22) Filed: Nov. 6, 2006

(65) Prior Publication Data

US 2009/0143787 A9    Jun. 4, 2009

(51) Int. Cl.
*A61B 17/00* (2006.01)
*B25J 17/00* (2006.01)

(52) U.S. Cl.
USPC .......... 606/130; 74/490.01; 606/1; 901/1

(58) Field of Classification Search
USPC .......... 414/4–8; 606/205–207, 130; 901/1–16, 901/19–20, 23–32; 74/490.01–490.09
See application file for complete search history.

(56) References Cited

U.S. PATENT DOCUMENTS

| | | | | |
|---|---|---|---|---|
| 4,555,217 A | * | 11/1985 | Wright | 414/735 |
| 4,762,455 A | * | 8/1988 | Coughlan et al. | 414/4 |
| 4,780,047 A | * | 10/1988 | Holt et al. | 414/730 |
| 4,828,453 A | * | 5/1989 | Martin et al. | 414/738 |
| 5,065,337 A | * | 11/1991 | Hara | 700/262 |
| 5,697,256 A | * | 12/1997 | Matteo | 74/490.04 |
| 5,710,870 A | * | 1/1998 | Ohm et al. | 700/263 |
| 6,296,635 B1 | * | 10/2001 | Smith et al. | 606/19 |
| 6,786,896 B1 | * | 9/2004 | Madhani et al. | 606/1 |
| 2004/0036438 A1 | * | 2/2004 | Yamagishi | 318/568.12 |

\* cited by examiner

*Primary Examiner* — Gary Jackson
*Assistant Examiner* — Richard Louis
(74) *Attorney, Agent, or Firm* — Young & Thompson

(57) ABSTRACT

A robotic surgical device for use in laparoscopic surgery, includes two robotic arms in parallel relationship with each other. Each arm has at least six joints providing a total of fourteen degrees of movement that accurately reproduce the movements of a human torso complete with arms. The robotic arms are connected to a support via a connection element.

7 Claims, 27 Drawing Sheets

ROBOTIC SURGICAL DEVICE

BACKGROUND OF THE INVENTION

A. Field of the Invention

The present invention is related to robotic surgical devices, and more particularly to a robotic surgical device for using in laparoscopic surgery which includes two robotic arms and a respective gripping tool each reproducing the natural movements of the human arm.

B. Description of the Related Art

The laparoscopic surgery systems available today including a robotic arm, have limited degrees of movement, which are reduced to simulate only some movements of the human wrist.

Said limited degree of movements limit the number of maneuvers that can be done during a surgery. Furthermore, the device that is introduced in the patients body normally have only one robotic arm at a distal portion, and since some procedures such as tissue cutting or suture procedures need at least two robotic arms, it is necessary to practice two or more incisions in patient's body in order to introduce an additional arm having a corresponding gripping tool thus complicating the whole surgery procedure.

Consequently, surgeons are required to take a training procedure which may take a time of one year in order to be qualified to operate a specific device.

There have been developed some devices which try to address the above referred problem such as U.S. patent application No. US2005/0096502, which describes "a robotic surgical device configured for performing minimally invasive surgical procedures. The robotic surgical device comprises an elongated body for insertion into a patient's body through a small incision. In one variation, the elongated body houses a plurality of robotic arms. Once the distal portion of the elongated body is inserted into the patient body, the operator may then deploy the plurality of robotic arms to perform surgical procedures within the patient's body. An image detector may be positioned at the distal portion of the elongated body or on one of the robotic arms to provide visual feedback to the operator of the device. In another variation, each of the robotic arms comprises two or more joints, allowing the operator to maneuver the robotic arms in a coordinated manner within a region around the distal end of the device".

Although the above referred device provides two parallel robotic arms, it doesn't describe a detailed implementation of the robotic arms for the device nor a specific preferred embodiment for a robotic arm including a specific number of joints, driving means, etc.

Therefore, applicant's developed a specific implementation of a robotic surgical device for using in laparoscopic surgery, including two robotic arms each having at least six joints providing a total of fourteen degrees of movement that accurately reproduce the movements of a human torso complete with arms.

Applicant's device includes a torso, two superior extremities each having a shoulder, arm, elbow, forearm, wrist and "hand".

Since applicant's device simulates the movements of the upper human extremities, it is easier for the surgeon to control the device since it can be maneuvered using the same movements learned during the standard training.

SUMMARY OF THE INVENTION

It is therefore a main object of the present invention to provide a robotic surgical device for using in laparoscopic surgery, including two robotic arms each having at least six joints.

It is another main object of the present invention to provide a robotic surgical device of the above disclosed nature which have least six joints providing a total of fourteen degrees of movement that accurately reproduce the movements of a human torso complete with arms.

It is a further object of the present invention to provide a robotic surgical device of the above disclosed nature which accurately reproduces the movements of a human torso complete with arms.

It is a further object of the present invention to provide a robotic surgical device of the above disclosed nature which simulates the movements of the upper human extremities, thus allowing the surgeon to control the device since it can be maneuvered using the same movements learned during the standard training.

These and other objects and advantages of the robotic surgical device of the present invention will become apparent to those persons having an ordinary skill in the art, from the following detailed description of the embodiments of the invention which will be made with reference to the accompanying drawings.

DETAILED DESCRIPTION OF THE INVENTION

Figure 1:
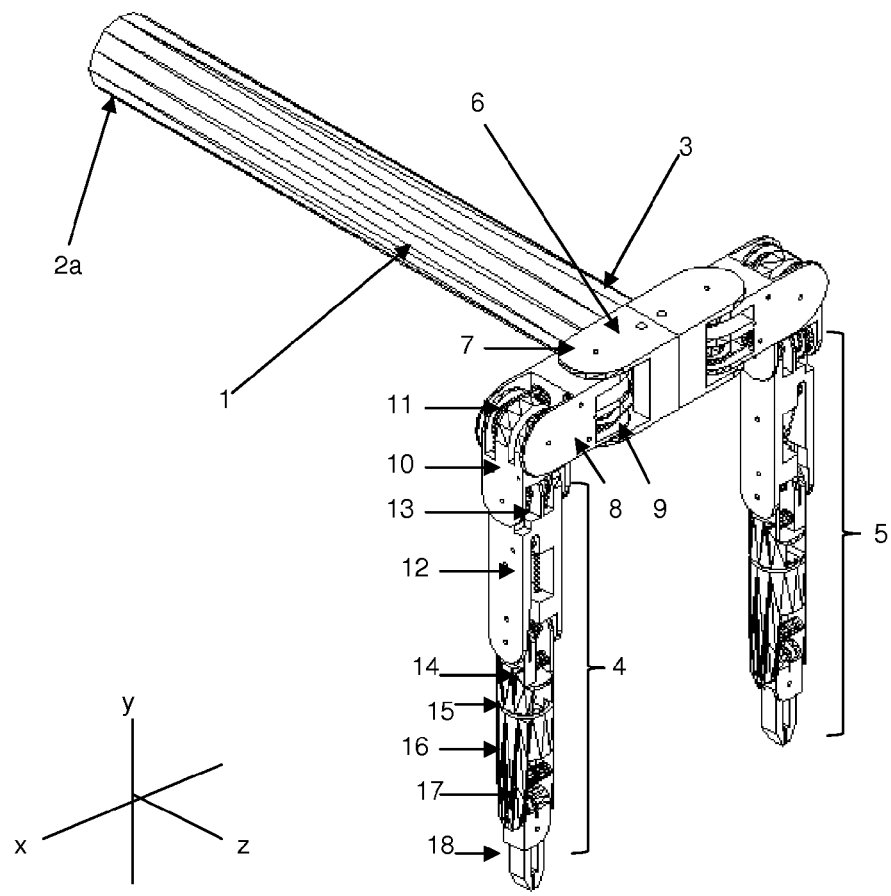
FIG. 1 is a perspective view of the robotical surgical device of the present invention including both robotic arms.
Figure 2:
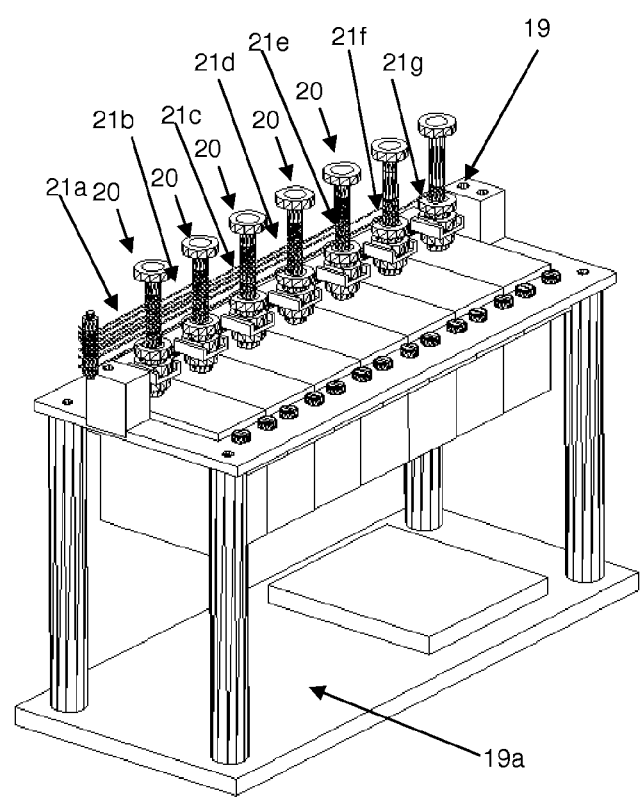
FIG. 2 is a perspective view of the seven stepper motors and movement transmission cables mounted over its base.

The robotical surgical device of the present invention will be described making reference to the X-Y-Z axis wherein the X axis corresponds to the left and right directions, the Y axis corresponds to the up and down directions and the Z axis corresponds to the front and rear directions.

Now the robotical surgical device will be described in accordance with its more general embodiment thereof, comprising:

support means comprising a long elongated and hollow member 1 having first 2a and a second 3 end;

a first 4 and a second 5 robotic arm each positioned in a parallel relationship from each other, each comprising:

a first connection element 6 fixedly attached to the second end of the support means having pivoting linking means 7, wherein the resting position for this element comprises a position parallel to the X axis;

a second connection element 8, pivotally linked to the pivoting linking means of the first connection element 6, said second connection element 8 able to pivot up to 90° to the front until reaching a position parallel to the Z axis and to a side until reaching a position parallel to the X axis, taking as reference the first connection element 6 resting position, having pivoting linking means 9 allowing a forward and backward pivoting movement and wherein the resting position comprises the position parallel to the X axis;

a third connection element 10, pivotally linked to the pivoting linking means of the second connection element, said third connection element 10 able to pivot up to 90° upwards until reaching a horizontal position parallel to the X axis and downwards until reaching a vertical position parallel to the Y axis, taking as reference the second connection element resting position, having pivoting linking means 11 allowing an upward and downward pivoting movement, and wherein the resting position comprises the position parallel to the Y axis;

a fourth connection element 12, pivotally linked to the pivoting linking means of the third connection element, said fourth connection element able to pivot up to 90° upwards until reaching a horizontal position parallel to the Z axis and downwards until reaching a vertical position parallel to the Y axis, taking as reference the third connection element resting position, having pivoting linking means 13 allowing an upward and downward pivoting movement, and wherein the resting position comprises the position parallel to the Y axis;

a fifth connection element 14, pivotally linked to the pivoting linking means of the fourth connection element, said fifth connection element able to pivot up to 90° upwards until reaching a horizontal position parallel to the Z axis and downwards until reaching a vertical position parallel to the Y axis, taking as reference the fourth connection element resting position, having rotating linking means 15 for linking an additional connection element, allowing concentric rotation over a single axis, and wherein the resting position comprises the position parallel to the Y axis;

a sixth connection element 16, rotary linked to the rotating linking means 15 of the fifth connection element 14, said sixth connection element 16 able to rotate 360° over its own axis, having pivoting linking means for linking a further element 17 allowing an upward and downward pivoting movement, and wherein the resting position for this element comprises the position parallel to the Y axis;

a gripping tool 18, pivotally linked to the pivoting linking means of the sixth connection element 16, said gripping tool 18 able to pivot up to 90° upwards until reaching a horizontal position parallel to the Z axis and downwards until reaching a vertical position parallel to the Y axis, taking as reference the sixth connection element resting position, and wherein the resting position for the gripping tool comprises the position parallel to the Y axis; and driving means connected to each connection element and gripping tool for driving each of the sixth connection elements and to open and close the gripping tool.

Thanks to the pivotal connections between each connection element, the gripping tool 18 of each robotic arm is able to move inside a very ample operational area, which mimics the functionality of a human torso including hands.

Figure 3:
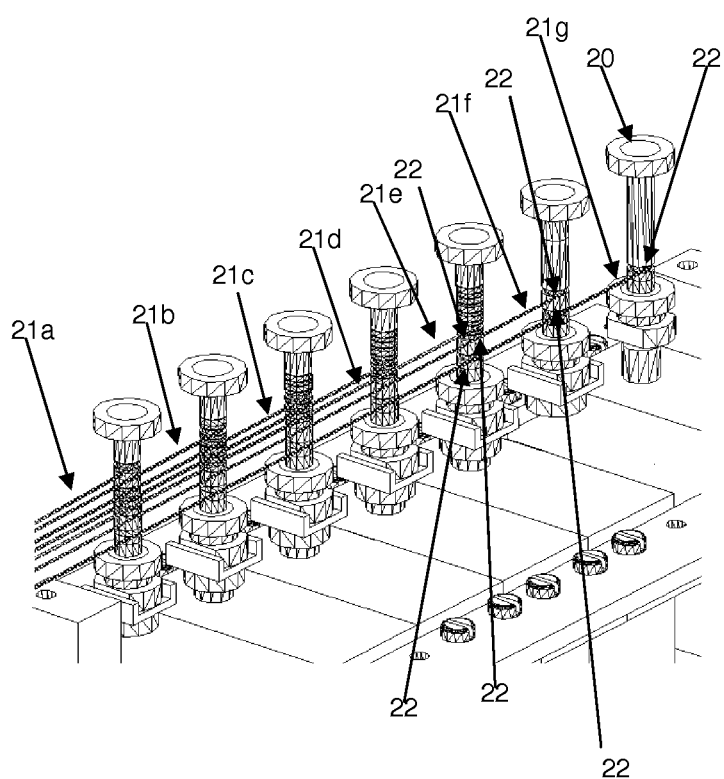
FIG. 3 is a close up perspective view of the seven stepper motors and movement transmission cables mounted over its base.
Figure 4:
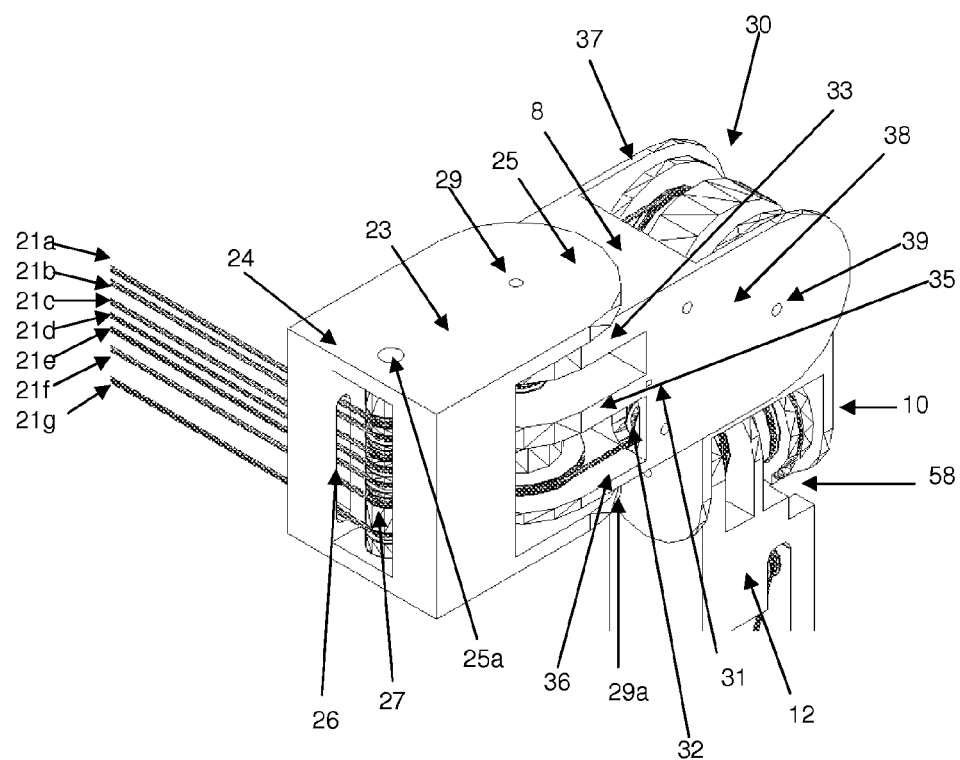
FIG. 4 is a close up perspective view of the first, second and third connection elements and movement transmission cables of the second robotic arm.
Figure 5:
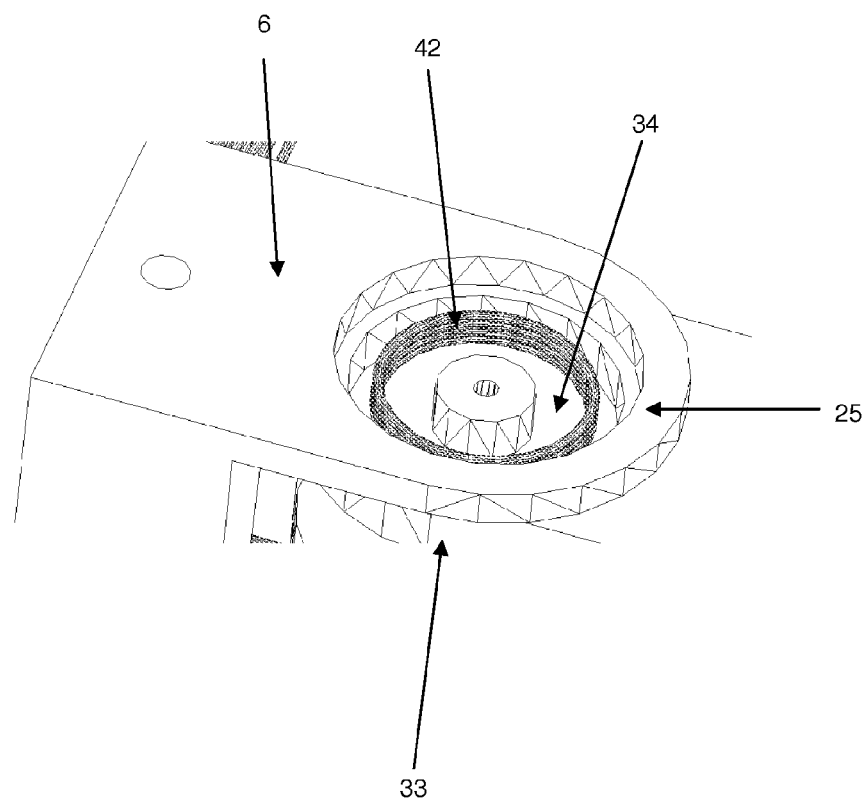
FIG. 5 is a partially disembodied view of the first connection element of the second robotic arm showing the circular spring.
Figure 6:
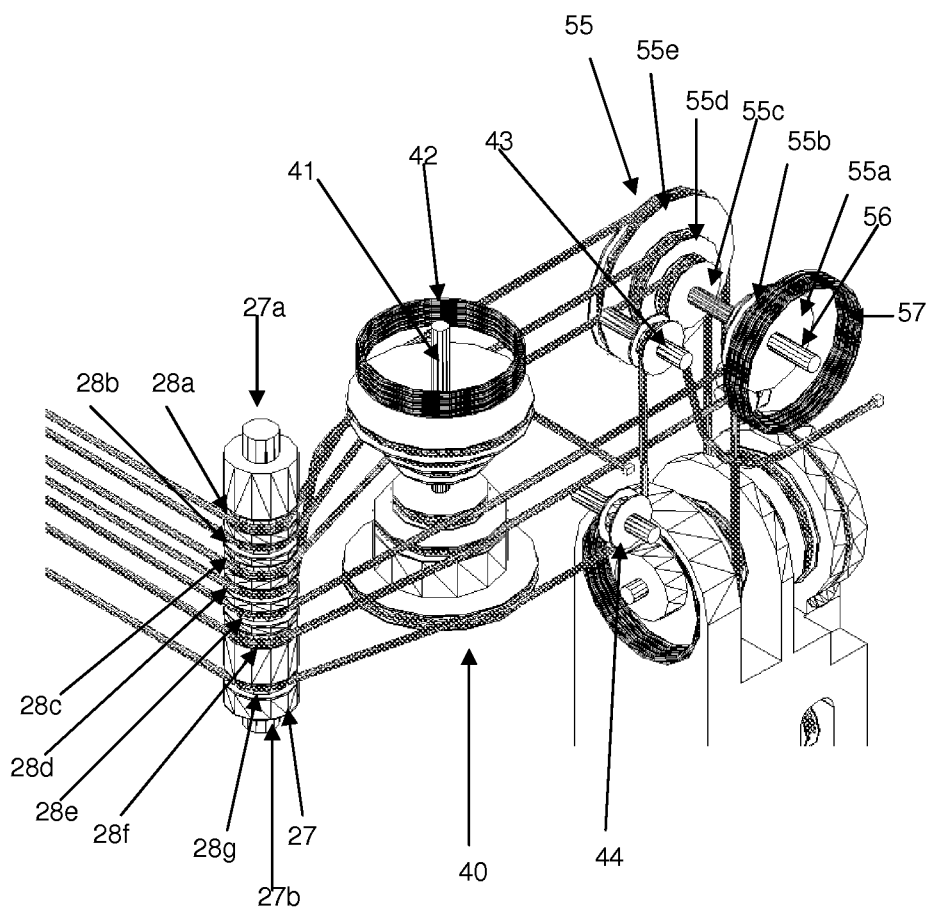
FIG. 6 is a close up disembodied perspective view of the first, second and third connection elements and movement transmission cables of the second robotic arm showing its internal components.
Figure 7:
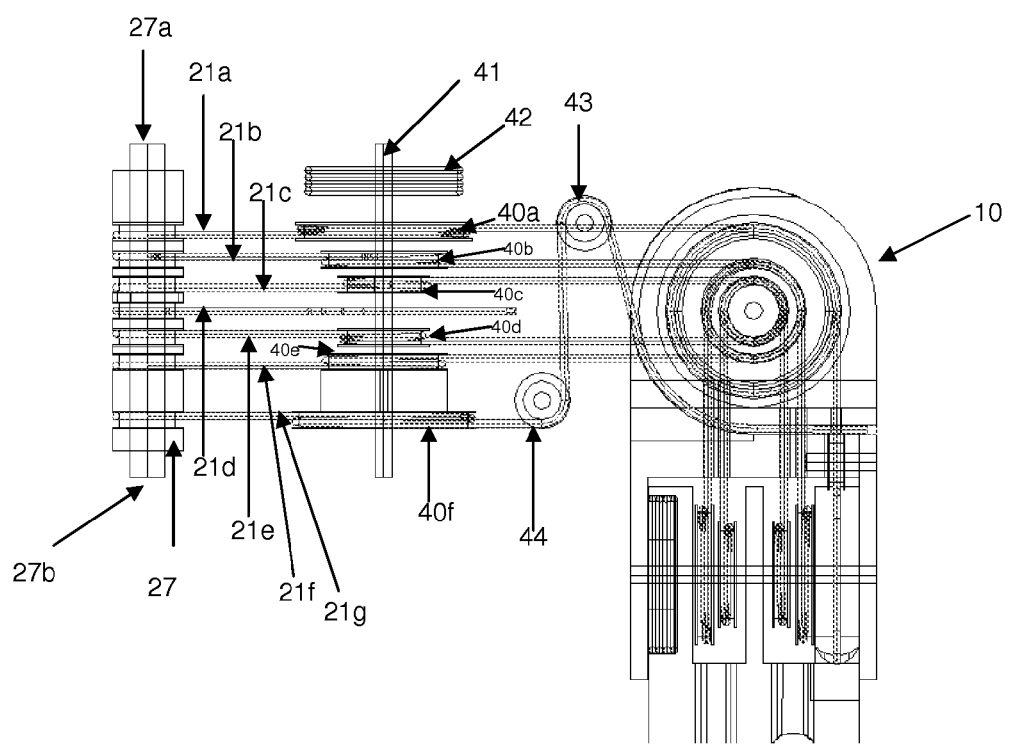
FIG. 7 is a is a close up disembodied frontal view of the first, second and third connection elements and movement transmission cables of the second robotic arm showing its internal components.
Figure 8:
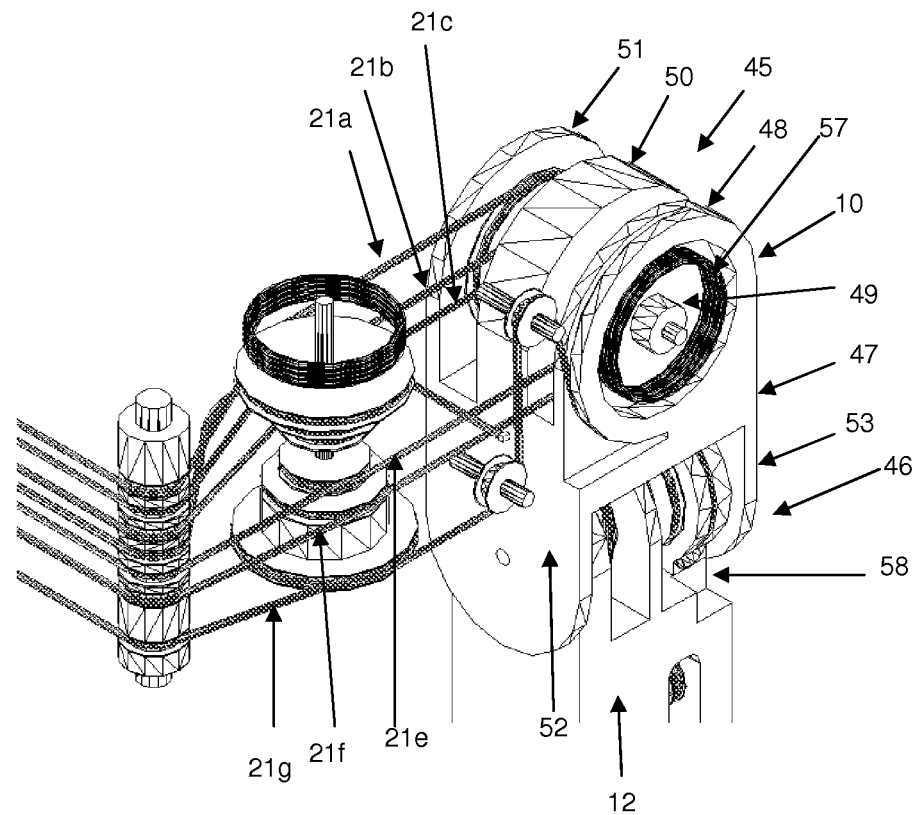
FIG. 8 is a close up partially disembodied perspective view of the first, second and third connection elements and movement transmission cables of the second robotic arm showing the internal components of the first and second connection element.
Figure 9:
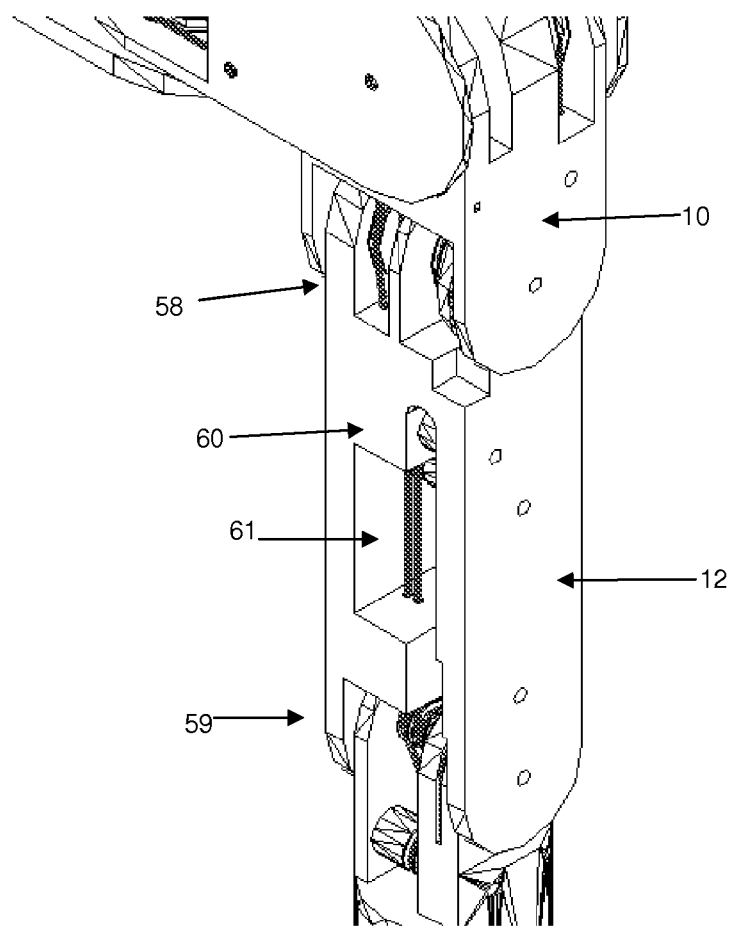
FIG. 9 is a close up perspective view of the third and fourth connection elements.
Figure 10:
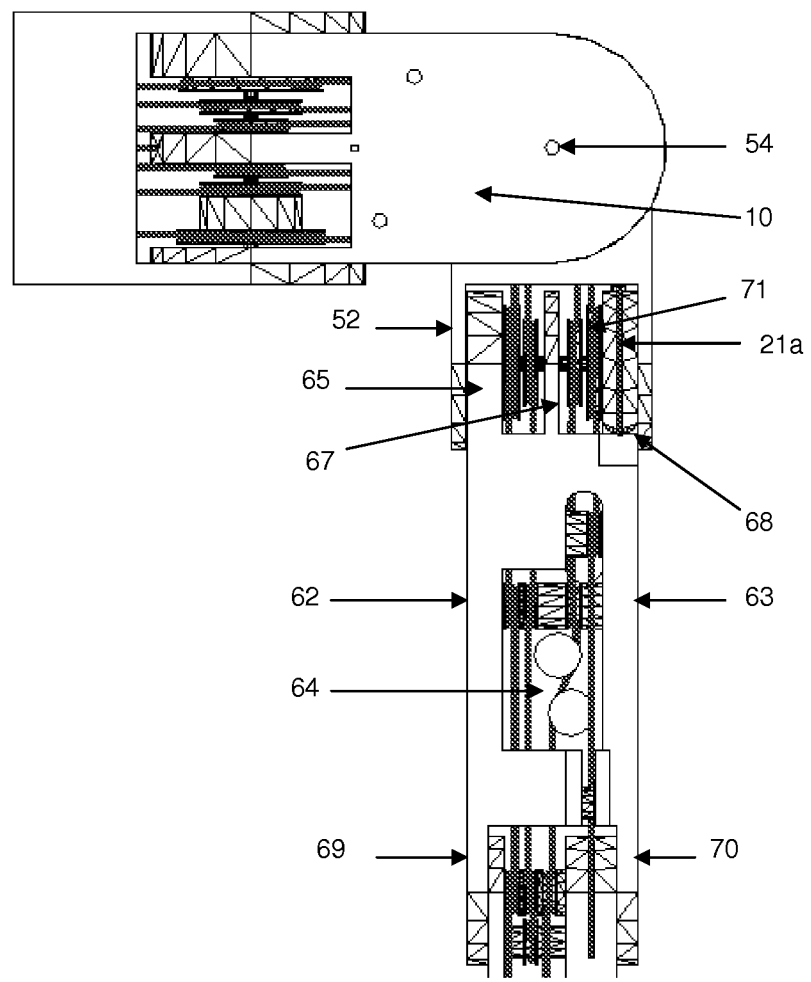
FIG. 10 is a close up front view of the third and fourth connection elements.
Figure 11:
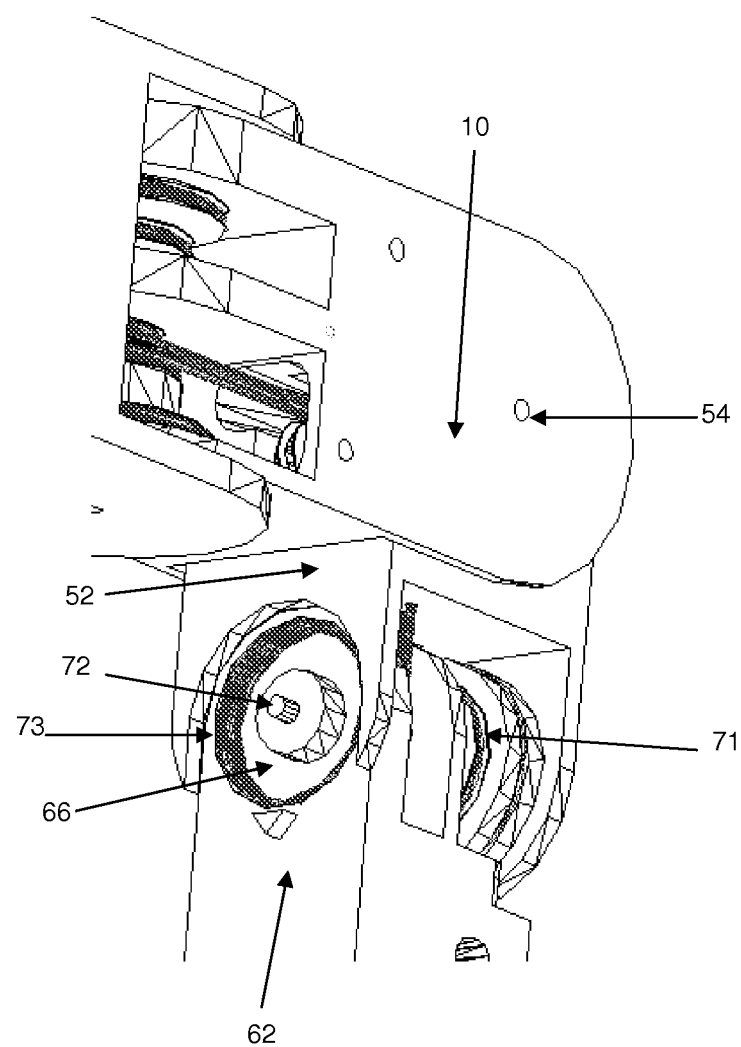
FIG. 11 is a close up partially disembodied perspective view of the third and fourth connection elements showing the circular spring of the fourth connection element.
Figure 12:
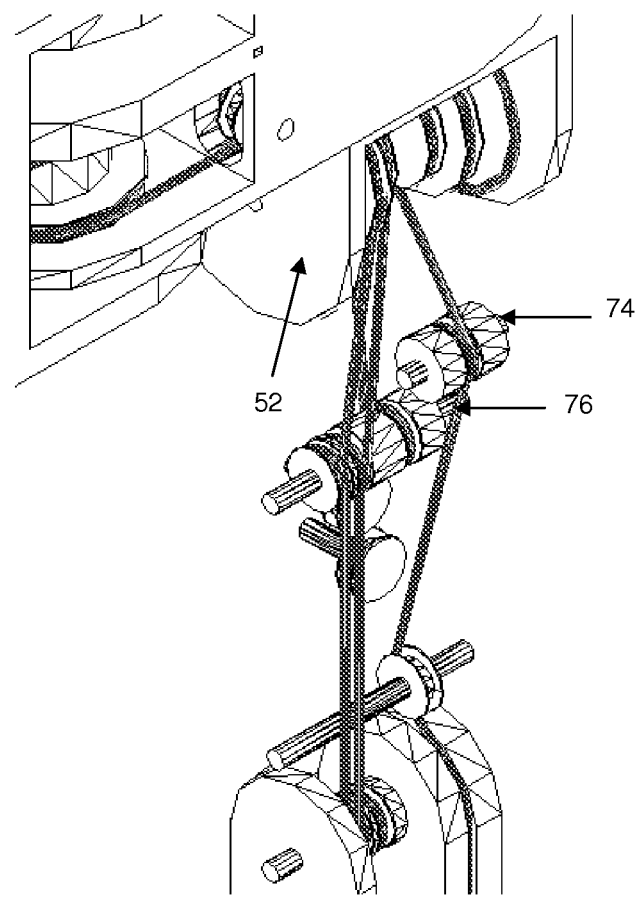
FIG. 12 is a close up partially disembodied perspective view of the third and fourth connection elements showing the internal components of the fourth connection element.
Figure 13:
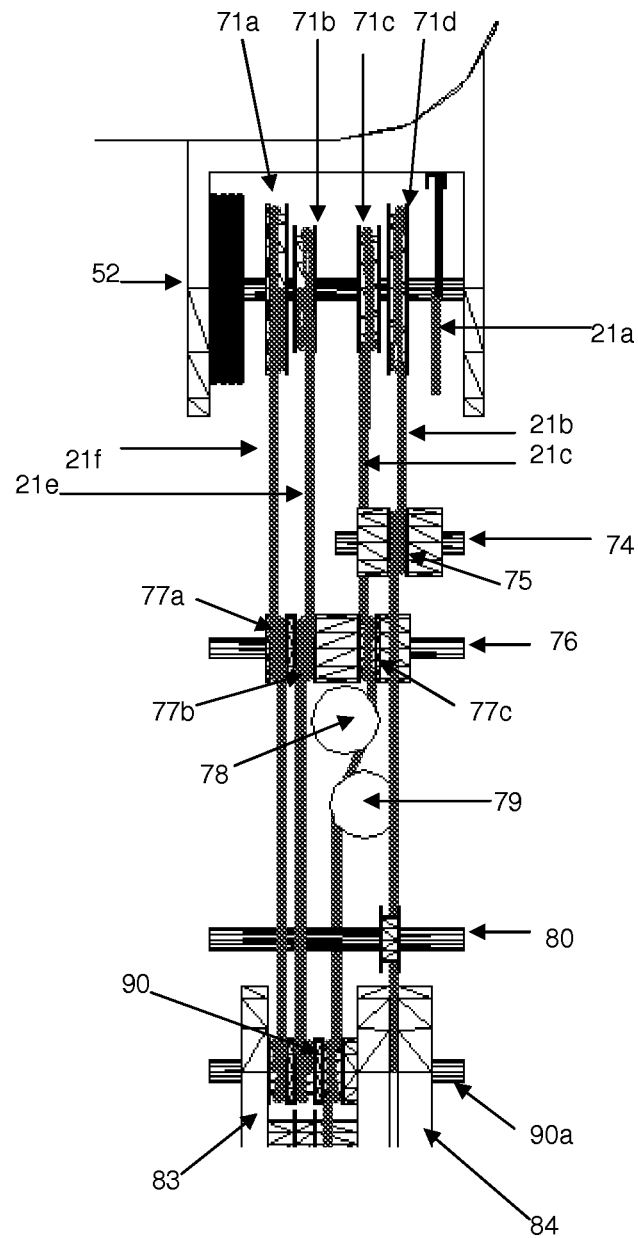
FIG. 13 is a close up partially disembodied frontal view of the third and fourth connection elements showing the internal components of the fourth connection element.
Figure 14:
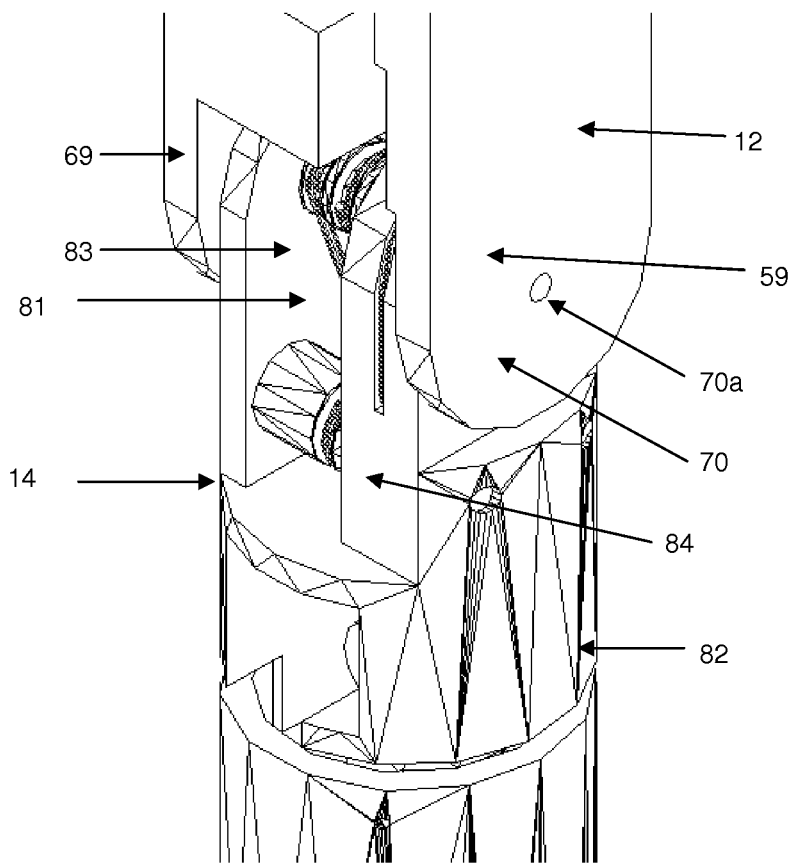
FIG. 14 is a close up perspective view of the fifth connection element connected to the fourth and sixth connection elements.
Figure 15:
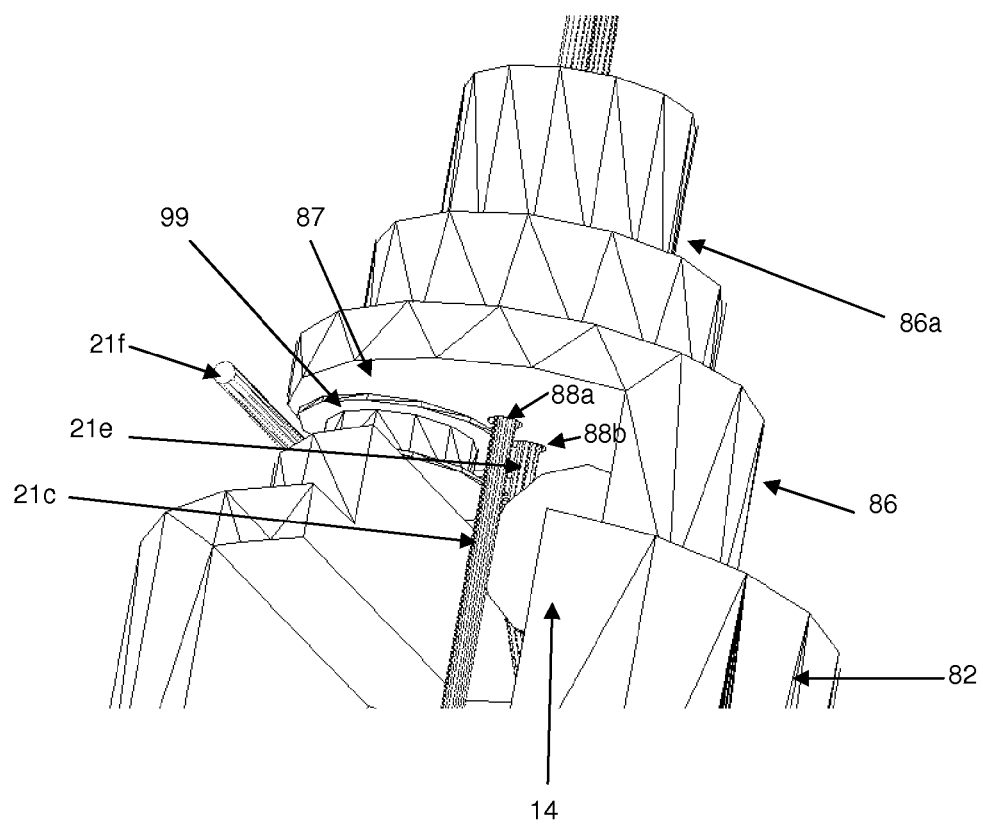
FIG. 15 is a close up perspective view of the fifth connection element showing the cylindrical linking member.
Figure 16:
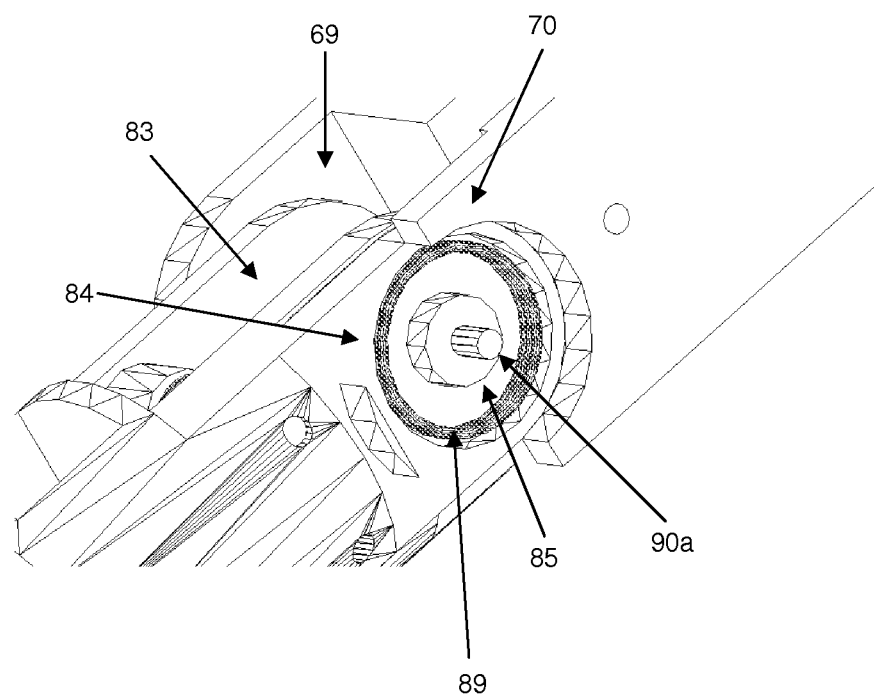
FIG. 16 is a close up partially disembodied perspective view of the fourth and fifth element showing the circular spring of the fifth connection element.
Figure 17:
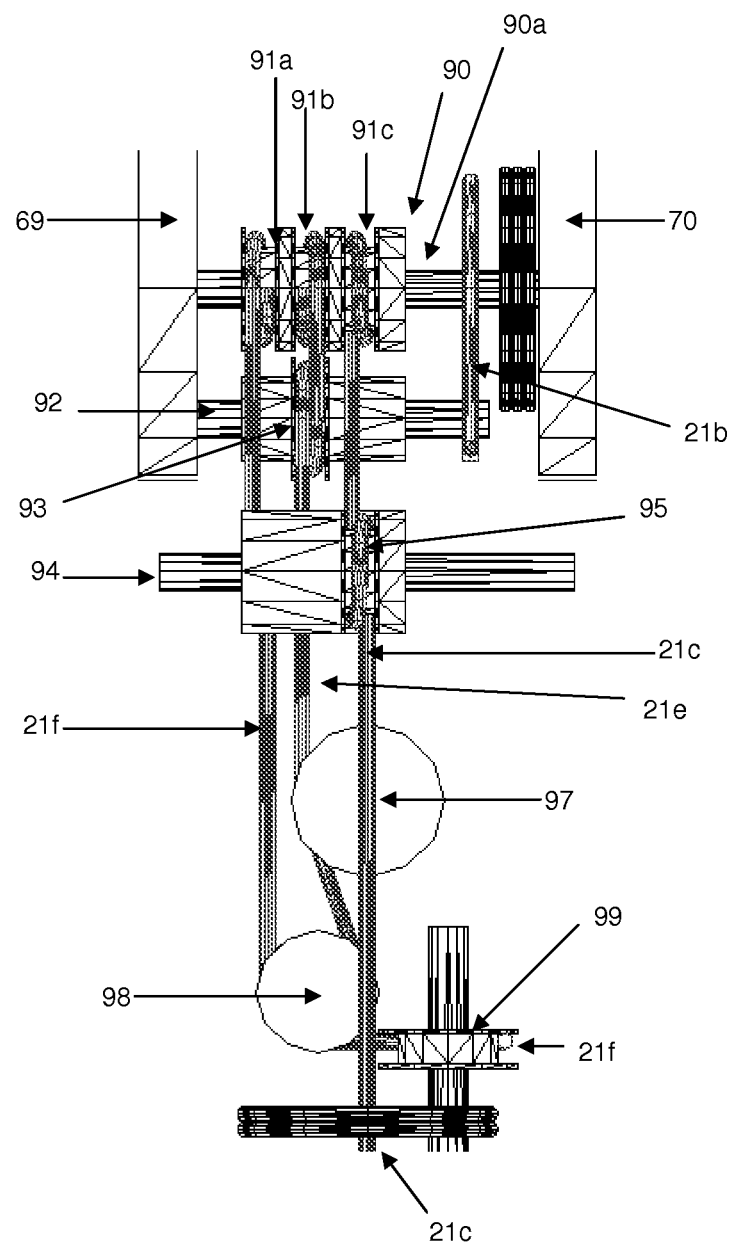
FIG. 17 is a close up disembodied front view of the fifth connection element showing its internal components.
Figure 18:
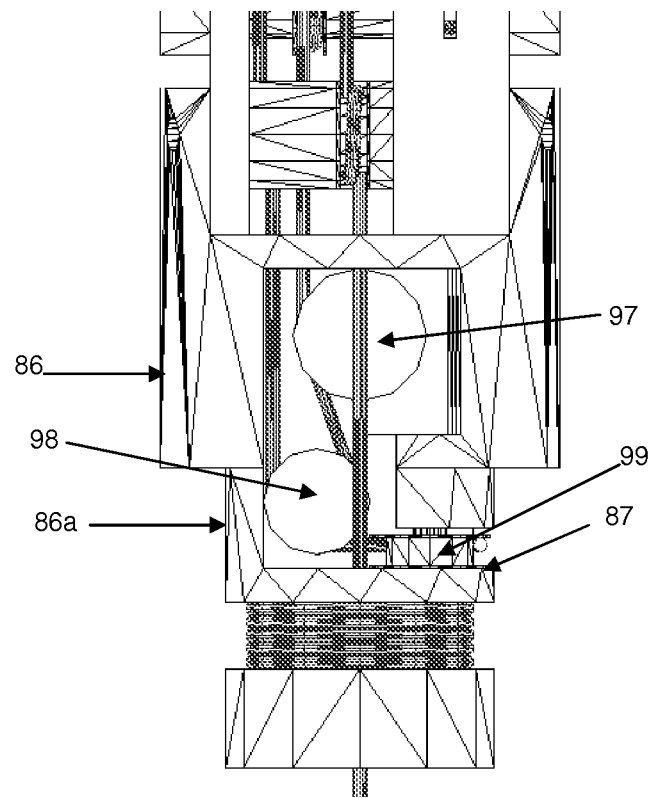
FIG. 18 is a close up frontal view of the second end of the fifth connection element partially showing its internal components.
Figure 19:
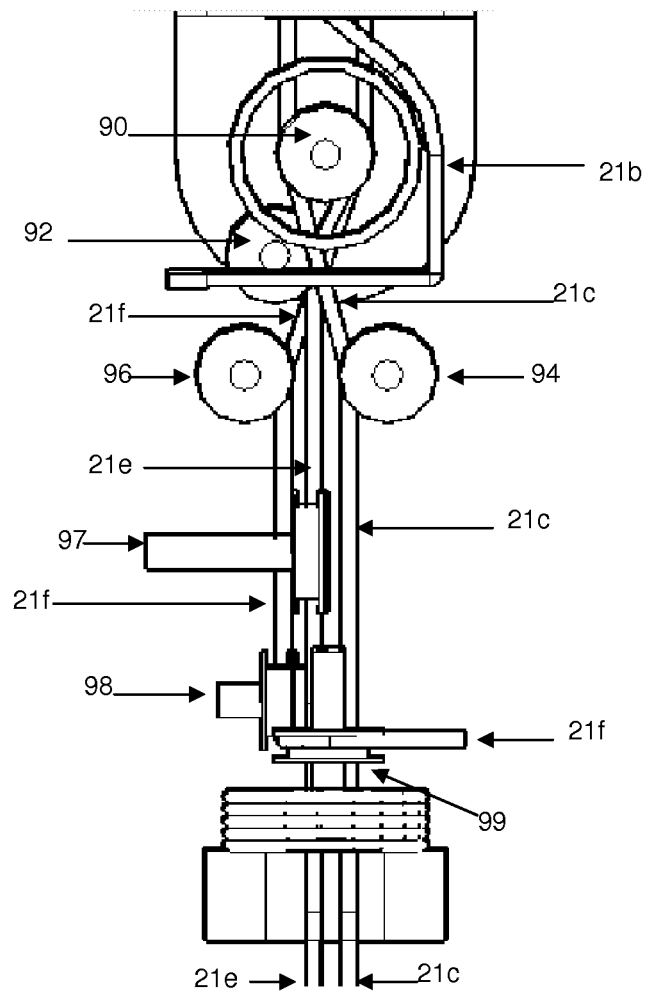
FIG. 19 is a close up left lateral disembodied view of the fifth connection element showing its internal components.
Figure 20:
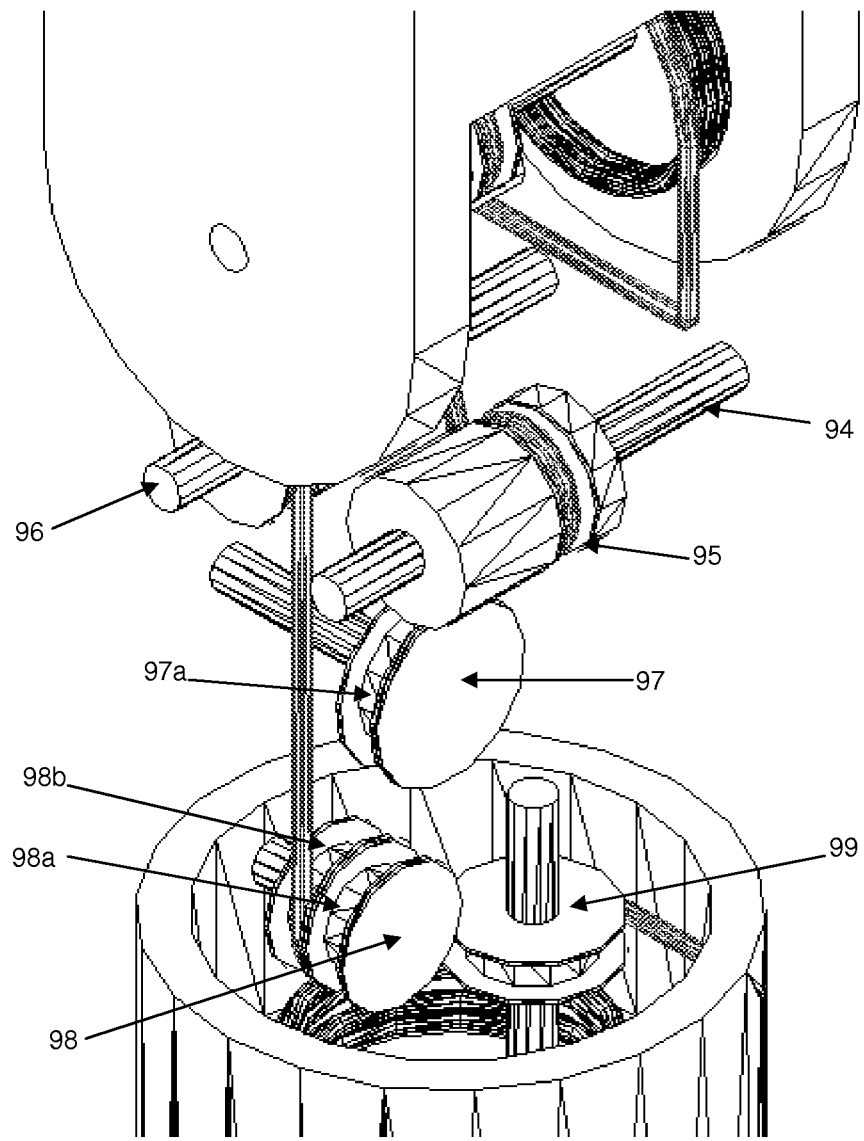
FIG. 20 is a close up partially disembodied perspective view of the fourth, fifth and sixth element showing the internal elements of the fifth connection element.
Figure 21:
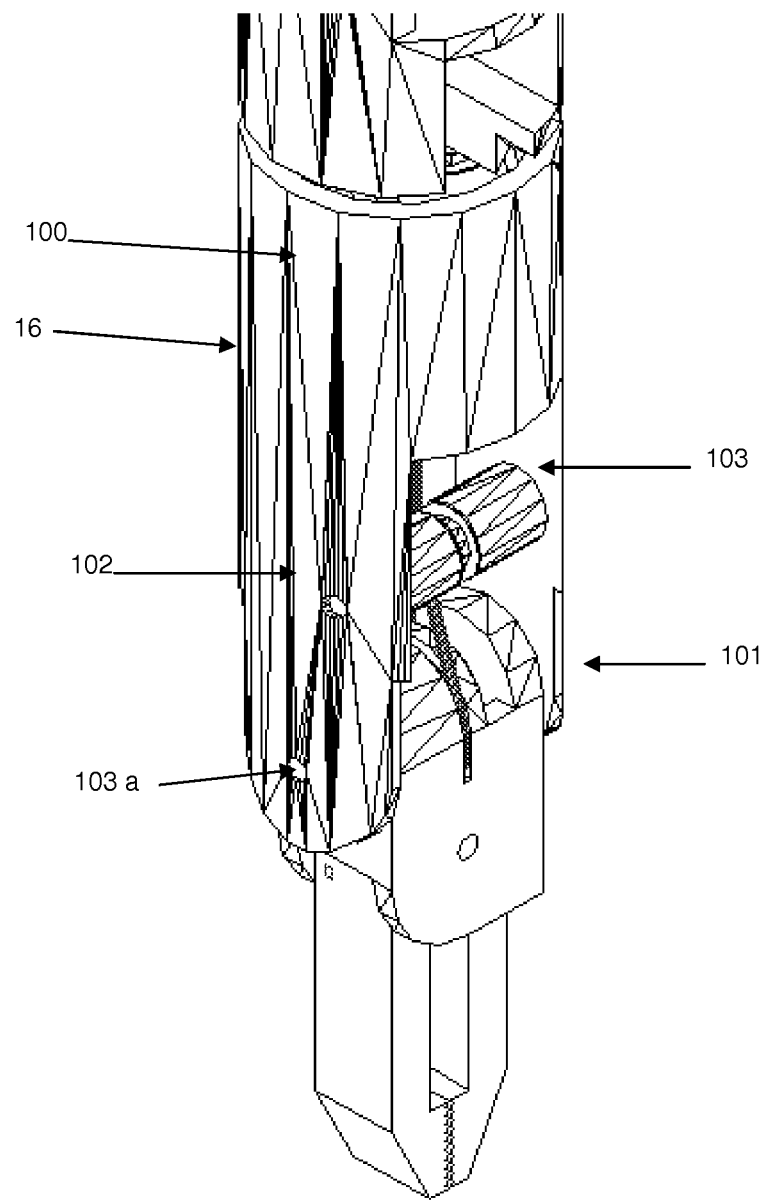
FIG. 21 is a close up left perspective view of the sixth connection element and gripping tool.
Figure 22:
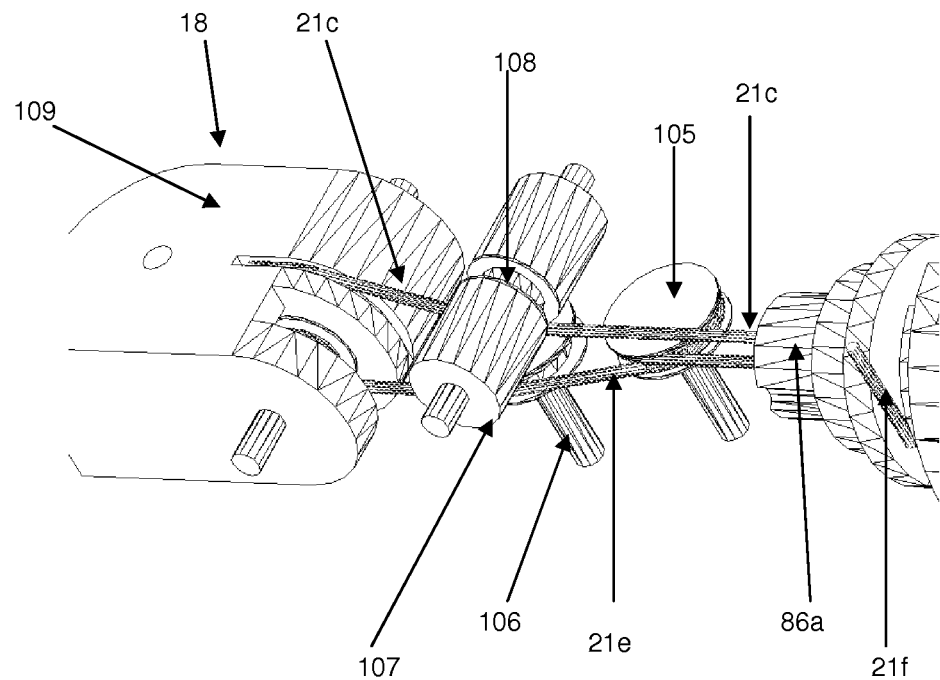
FIG. 22 is a close up perspective partially disembodied view of the fifth, sixth and gripping tool showing the internal components of the sixth connection element.
Figure 23:
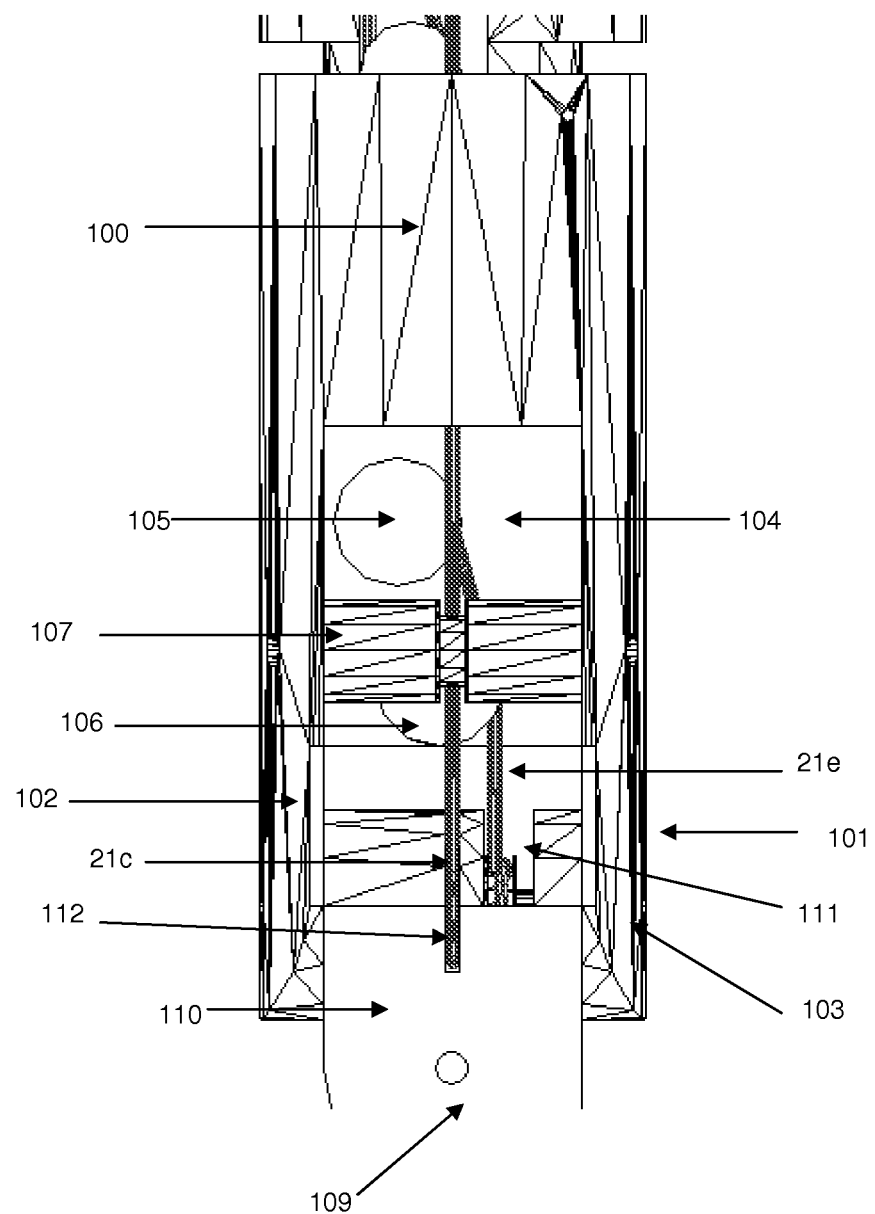
FIG. 23 is a close up frontal view of the sixth connection element and griping tool partially showing the internal elements of the sixth connection element.
Figure 24:
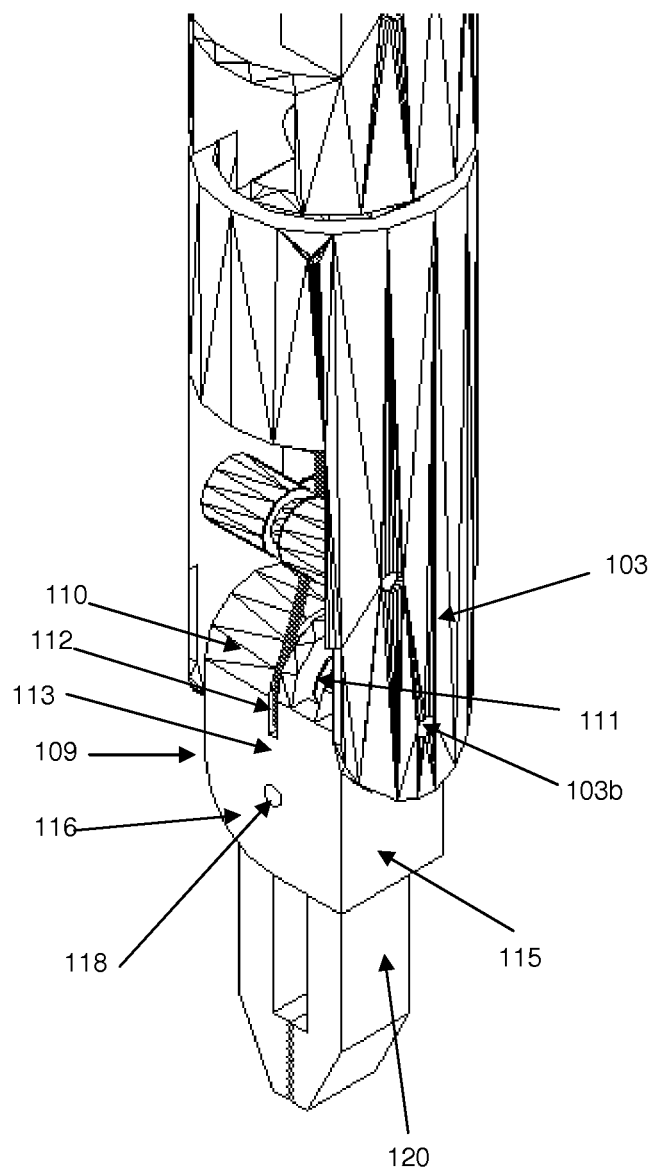
FIG. 24 is a close up right perspective view of the sixth connection element and gripping tool.
Figure 25:
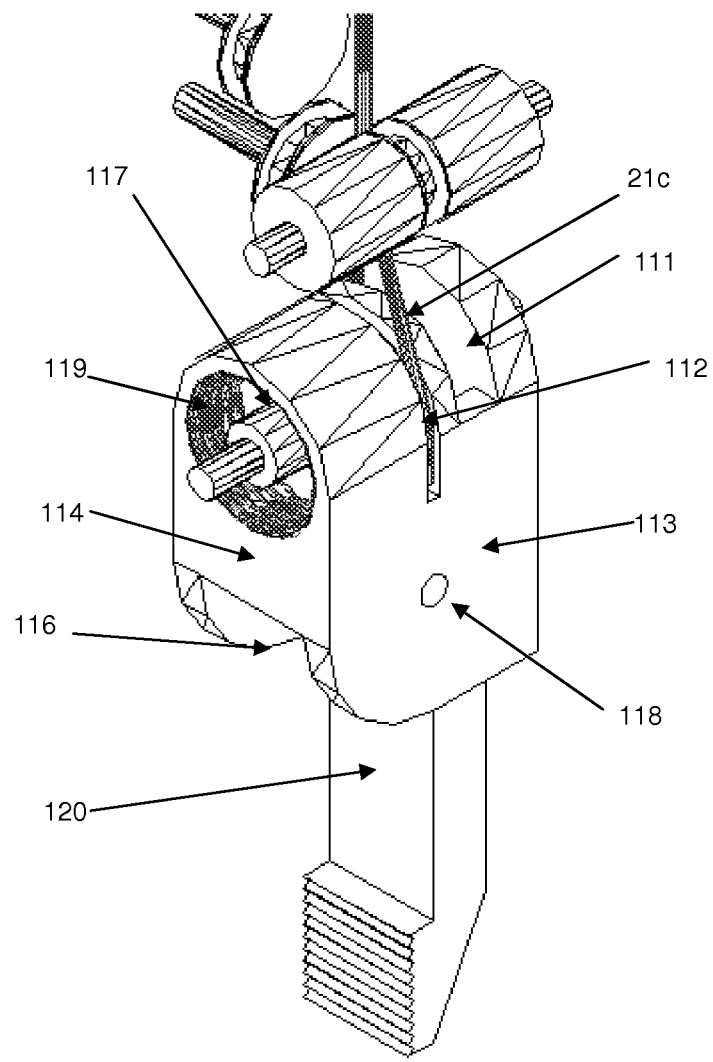
FIG. 25 is a close up partially disembodied perspective view of the sixth connection element and gripping tool lacking the fixed plier showing the internal components of the second end of the sixth connection element, and the circular spring located at a first end of the gripping tool hollow main body.
Figure 26:
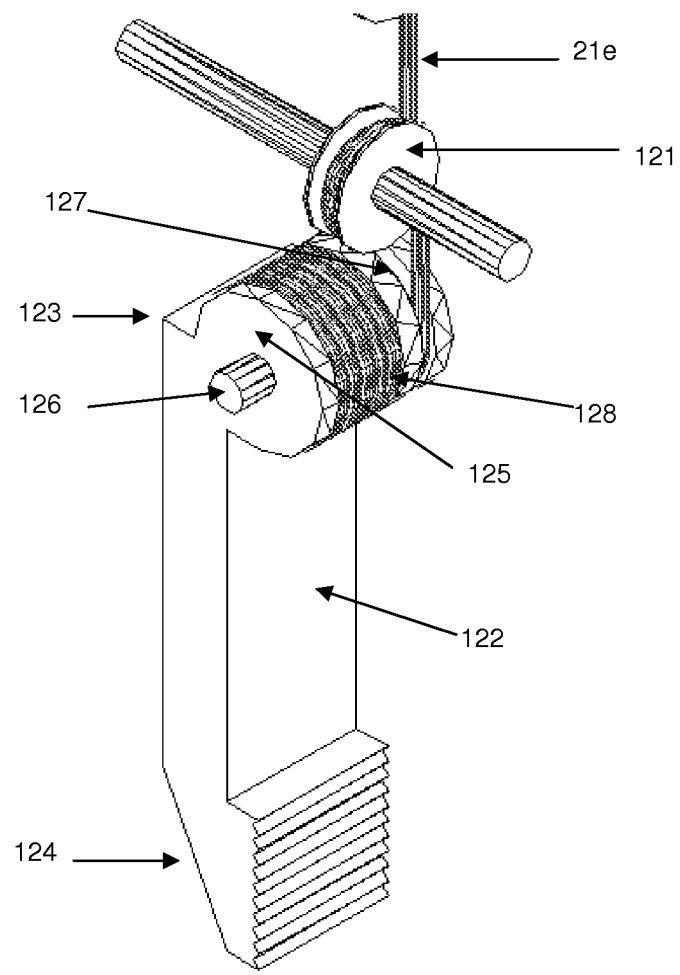
FIG. 26 is a close up disembodied perspective view of the gripping tool showing only the fixed plier and its internal components.

Now the robotical surgical device of the present invention will be described making reference to a preferred embodiment thereof, comprising:

support means comprising an elongated hollow cylinder 1 having a first 2a and a second end 3 and having a diameter size adequate for entering through a standard sized laparoscopic surgical opening;

a first 4 and a second 5 robotic arm each positioned in a parallel relationship from each other;

driving means for driving both robotic arms, comprising: a first 19 and a second group (not shown) of seven stepper motors, each group attached to a base 19*a* and driving a correspondent robotic arm, wherein the motors of each group are aligned in two parallel rows and wherein each motor drives a rotary pulley 20 located at a superior portion thereof;

movement transmission means for each stepper motor, each comprising a cable (21*a*, 21*b*, 21*c*, 21*d*, 21*e*, 21*f*, 21*g*) attached to the pulley of a respective motor for a total of fourteen cables (only seven shown) divided in two groups of seven cables, each group corresponding to a robotic arm 4, 5, wherein each of the cables attached to its respective pulley 20, passes by a correspondent series of circular grooves 22, each located at subsequent pulleys 20, thus lineally guiding each cable along subsequent pulleys 20 so that a first pulley has one circular groove, the second pulley has two circular grooves, one for its own cable and one for the passing cable of the previous pulley 20 and so on, thus avoiding the entanglement of the cables as shown in FIG. 3, and wherein each cable is pulled when the pulley 20 rotates in one direction and is loosen when the pulley 20 rotates in an opposed direction, and wherein both groups of cables are aligned and conducted through the elongated cylinder 1 entering a first end 2*a* and exiting through the second end 3 thereof;

wherein each robotic arm comprising:

a first connection element 6 comprising a hollow quadrangular member having a first 23 and a second (not shown) longitudinal wall, a central longitudinal axis, a first end 24 and a second open rounded end 25, including a first 25*a* and a second (not shown) pin holes located at each longitudinal wall near the first end 24 of the first connection element 6, a rectangular aperture 26 at a lateral side near the first end 24, said first connection element 6 been fixedly attached to the second end 3 of the hollow elongated cylinder 1 in such way that its longitudinal axis is located perpendicularly to the hollow cylindrical tube and the lateral rectangular aperture 26 coincide with the second end 3 of the hollow cylindrical tube 1 and having:

a rotating sluing drum 27 including a pin 27*a*, 27*b* at each end, each pin rotary received inside the pin holes 25*a* so that the ends of the first rotary sluing drum 27 are rotary linked to both longitudinal walls 23 and located between them inside the first connection element 6 near its first end 24 and aligned with its central longitudinal axis, having seven concentric circular grooves 28*a*, 28*b*, 28*c*, 28*d*, 28*e*, 28*f*, 28*g*;

a first 29 and a second (not shown) opposed pin holes each located at a correspondent longitudinal wall 23 near the second end 25 of the first connection element 6, each aligned with the central longitudinal axis;

wherein the first corresponding group of cables 21*a*, 21*b*, 21*c*, 21*d*, 21*e*, 21*f*, 21*g* enter the first connection element 6 through the rectangular aperture 26, each passing by the sluing drum 27 and guided by a respective concentric circular groove 28*a*, 28*b*, 28*c*, 28*d*, 28*e*, 28*f*, 28*g* and exiting the first connection element 6 through the second open end 25; and wherein the resting position for this element comprises a position parallel to the X axis;

a second connection element 8 including a first open end 29*a* and a second open end 30, and a central portion 31 including a first (not shown) and a second 32 passage, wherein the first end 29*a* including a superior rounded longitudinal wall 33 having a central superior circular recess 34, a central rounded longitudinal wall 35, and an inferior rounded longitudinal wall 36, each depending from the central portion 31 and each including a central coincident pin hole (not shown), wherein the pin hole of the superior rounded longitudinal wall 33 is located at a central portion of the circular recess 34 and wherein the second open end 30 includes a first rounded lateral wall 37 and a second opposed rounded lateral wall 38 each extending from the central portion 31 and each respectively having a first (not shown) and a second 39 pin hole at a central portion thereof, said second connection element 8 further having:

six pulleys 40 having a central perforation (not shown), each one located below the other forming a vertical row, and wherein a first 40*a*, second 40*b* and third pulley 40*c* are located and rotary retained between the superior rounded longitudinal wall 33 and the central rounded longitudinal wall 35, and a fourth 40*d*, fifth 40*e* and sixth 40*f* pulley are located and rotary retained between the central rounded longitudinal wall 35 and the inferior 36 rounded longitudinal wall;

a pin 41 passing through the pin hole of the superior rounded longitudinal wall 33, through the central perforation of the first 40*a*, second 40*b* and third 40*c* pulley, through the pin hole of the central rounded longitudinal wall 35, through the central perforation of the fourth 40*d*, fifth 40*e* and sixth 40*f* pulley and through the pinhole of the inferior rounded longitudinal wall 36, thus rotary retaining the six pulleys 40 and wherein the pin protrudes over the pinhole of the superior rounded longitudinal wall 33 and below the inferior rounded longitudinal wall 36;

a circular spring 42 tightly received inside the circular recess 34 located at the superior rounded longitudinal wall 33;

wherein a first 21*a*, second 21*b* and third 21*c* cable exiting the first connection element 6 each enters the second connection element 8 through the first open end 29*a* and passes by and surrounds a correspondent first 40*a*, second 40*b* and third 40*c* pulley and are guided through the first passage of its central portion 31 to the second open end 30 through which they exit the second connection element 8 and wherein a fifth 21*e*, sixth 21*f*, and seventh 21*g* cable exiting the first connection element 6, enters the second connection element 8 through the first open end 29*a* and passes by and surrounds a correspondent fourth 40*d*, fifth 40*e* and sixth 40*f* pulley and are guided through the second passage 32 of its central portion 31 to the second open end 30 through which they exit the second connection element 8;

wherein a fourth cable 21*d* is linked to the central portion 31 of the second connection element 8, thus connecting the second connection element 8 directly to a fourth stepper motor, thus driving the second connection element 8;

wherein the second connection 8 element is pivotally retained inside the second open rounded end 25 of the first 6 connection element by locking the portions of the pin 41 protruding over the superior rounded longitudinal wall 33 and below the inferior rounded longitudinal 36 wall inside the first 29 and second pin holes located at a correspondent longitudinal wall 23, 25 of the first connection element 6 in such way that the whole first end 29*a* of the second connection element 8 including the superior 33, central 35 and inferior 36 rounded longitudinal walls and pulleys 40 are retained between the first 23 and second longitudinal walls in such way that said second connection element 8 is able to pivot up to 90° to the front until reaching a position parallel to the Z axis and to a side until reaching a position parallel to the X axis, taking as reference the first connection element 6 resting position, when the fourth stepper motor pulls the fourth cable 21d linked to the second connection element 8 and wherein the resting position for this element comprises the position parallel to the X axis;

wherein the circular spring 42 remains tightly retained between the first longitudinal wall 23 inferior portion of the first connection element 6 and the circular recess 34 of the superior rounded longitudinal wall 33 of the second connecting element 8 thus applying a torsional force over said two elements, forcing the second connecting element 8 to return to its resting position; and further including a first 43 and a second 44 lateral pulley each respectively linked at a superior and inferior portion of the first 37 and second 38 rounded lateral wall between them and inside the second open end 30 of the second connection element 8, and wherein the seventh cable 21g passing through the second passage 32 passes by said first 43 and second 44 lateral pulley before emerging from the second connection element 8 by the second open end 30;

a third connection element 10 including a first open end 45 and a second open end 46, and a central portion 47 including a first and a second passage (not shown) wherein the first end 45 including a first rounded longitudinal wall 48 having a central superior circular recess 49, a central rounded longitudinal wall 50, and an third rounded longitudinal wall 51, each depending from the central portion 47 and each including a central coincident pin hole (not shown), wherein the pin hole of the first rounded longitudinal wall 48 is located at a central portion of the circular recess 49 and wherein the second open end 46 includes a first rounded lateral wall 52 and a second rounded lateral wall 53 each extending from the central portion 47 and including a correspondent first 54 and a second (not shown) pin holes, and having:

five pulleys 55 having a central perforation (not shown), each one located below the other forming a linear row, and wherein a first 55a and second 55b pulley are located and rotary retained between the first rounded longitudinal wall 48 and the central rounded longitudinal wall 50, and a third 55c, fourth 55d and fifth 55e pulley are located and rotary retained between the central rounded longitudinal wall 50 and the third rounded longitudinal wall 51;

a pin 56 passing through the pin hole of the first rounded longitudinal wall 48, through the central perforation of the first 55a and second 55b pulley, through the pin hole of the central rounded longitudinal wall 50, through the central perforation of the third 55c, fourth 55d and fifth 55e pulley and through the pinhole of the third rounded longitudinal wall 51 in that order, thus rotary retaining the five pulleys 55 and wherein the pin 56 protrudes over the pinhole of the first rounded longitudinal wall 48 and below the third rounded longitudinal wall 51;

a circular spring 57 tightly received inside the circular recess 49 located at the first rounded longitudinal wall 48;

wherein a fifth 21e, and a sixth 21f cable exiting the second connection element 8 each enters the third connection element 10 through the first open end 45 and passes by and surrounds a correspondent second 55b, and first 55a pulley and are guided through the first passage of its central portion 47 to the second open end 46 through which they exit the third connection element 10 and wherein a first 21a, second 21b and third 21c cable exiting the second connection element 8, enters the third connection element 10 through the first open end 45 and passes by and surrounds a correspondent fifth 55e, fourth 55d and third 55c pulley and are guided through the second passage of its central portion 47 to the second open end 46 through which they exit the third connection element 10;

wherein a seventh cable 21g is linked to the central portion 47 of the third connection element 10, thus connecting the third connection element directly to a seventh stepper motor, thus driving the third connection element 10;

wherein the third connection element 10 is pivotally retained inside the second open end 30 of the second connection element 10 by locking the portions of the pin 56 protruding over the first rounded longitudinal wall 48 and below the third rounded longitudinal wall 51 inside the first and second 39 pin hole located at a correspondent second open end 30 rounded lateral wall 37, 38 of the second connection element 8 in such way that the whole first end 45 of the third connection element including the first 48, central 50 and third 51 rounded longitudinal walls and pulleys 55 are retained between the first 37 and second 38 rounded longitudinal walls in such way that said third connection element 10 is able to move up to 90° upwards until reaching a horizontal position parallel to the X axis and downwards until reaching a vertical position parallel to the Y axis, taking as reference the second connection element 8 resting position, when the seventh stepper motor pulls the seventh cable 21g linked to the third connection element 10 and wherein the resting position comprises the position parallel to the Y axis; and wherein the circular spring 57 remains tightly retained between an internal face of the second rounded lateral wall 38 of the second connection element 8 and the circular recess 49 of the first rounded longitudinal wall 48 of the third connecting element 10 thus applying a torsional force over said two elements, forcing the third connecting element 10 to return to its resting position;

a fourth connection element 12 including a first open end 58 and a second 59 open end, and an elongated central portion 60 including a first and a second passage (not shown) and a central path 61 having a longitudinal axis defined by a first 62 and a second 63 lateral wall and by an "inferior" longitudinal wall 64, wherein the first end 58 including a first rounded lateral wall 65 having a central superior circular recess 66, a central rounded lateral wall 67, and an third rounded lateral wall 68, each depending from the central portion 60 and each including a central coincident pin hole (not shown), wherein the pin hole of the superior rounded longitudinal wall is located at a central portion of the circular recess 66 and wherein the second open end 59 includes a first rounded lateral wall 69 and a second rounded lateral wall 70 extending from the central portion each having a central pin hole 70a (only the pin hole of the second rounded lateral wall 70 shown), and having:

four pulleys 71 having a central perforation (not shown), each one located below the other forming a linear row, and wherein a first 71a and a second pulley 71b are located and rotary retained between the first end 58 first rounded lateral wall 65 and the first end central rounded longitudinal wall 67, and a third 71c and fourth 71d pulley are located and rotary retained between the first end central rounded longitudinal wall 67 and the first end third rounded longitudinal wall 68;

a pin 72 passing through the pin hole of the first end first rounded longitudinal wall 65, through the central perforation of the first 71a and second 71b pulley, through the pin hole of the first end central rounded longitudinal wall 67, through the central perforation of the third 71c and fourth pulley 71d and through the pinhole of the first end third rounded longitudinal wall 68 in that order, thus rotary retaining the four pulleys 71 and wherein the pin 72 protrudes over the first end first rounded longitudinal wall 65 and below the first end third rounded longitudinal wall 68;

a circular spring 73 tightly received inside the circular recess 66 located at the first end first rounded longitudinal wall 65;

wherein a sixth 21f and fifth 21e cable exiting the third connection element 10 each enters the fourth connection element 12 through the first open end 58 and passes by and surrounds a correspondent first 71a and second 71b pulley and are guided through the first passage of the central portion 60 across the central path 61 to the second open end 59 through which they exit the fourth connection element 12 and wherein a second 21b and third 21c cable exiting the third connection element 10, enters the fourth connection element 12 through the first open end 58 and passes by and surrounds a correspondent fourth 71d and third 71c pulley and are guided through the first passage of the central portion 60 across the central path 61 to the second open end 59 through which they exit the fourth connection element 12;

wherein a first cable 21a is linked to the first end third rounded lateral wall 68 of the fourth connection element, thus connecting the fourth connection element directly to the first stepper motor, thus driving the fourth connection element;

wherein the fourth connection element 12 is pivotally retained inside the second open end 46 of the third connection element 10 by locking the portions of the pin 72 protruding over the first end first rounded lateral wall 65 and below the first end third rounded longitudinal wall 68 inside the first 54 and second pin holes located at a correspondent second open end first 52 and second 53 rounded lateral wall of the third connection element 10 in such way that the whole first end 58 of the fourth connection element 12 including the first 65, central 67 and third 68 rounded longitudinal walls and pulleys 71 are retained between the second end first 52 and second 53 longitudinal walls in such way that said fourth connection element 12 is able to move up to 90° upwards until reaching a horizontal position parallel to the Z axis and downwards until reaching a vertical position parallel to the Y axis, taking as reference the third connection element 10 resting position, when the first stepper motor pulls the first cable 21a linked to the fourth connection element 12 and wherein the resting position for the fourth connection element 12 comprises the position parallel to the Y axis;

wherein the circular spring 73 remains tightly retained between an internal face of the second end first rounded lateral wall 52 of the third connection element 10 and the circular recess 66 of the first end first rounded lateral wall 65 of the fourth connecting element 12 thus applying a torsional force over said two elements, forcing the fourth connecting element 12 to return to its resting position; and further including:

a first sluing drum 74 having a first and a second end, and a longitudinal axis, wherein said first sluing drum is rotary and transversally retained inside the central path 61 in such way that both ends are rotary retained between the lateral walls 62, 63 of the central path 61 with its longitudinal axis being located perpendicularly to the central path longitudinal axis and having one circular groove 75;

a second sluing drum 76 having a first and a second end, and a longitudinal axis, wherein said second sluing drum 76 is rotary and transversally retained inside the central path 61 in such way that both ends are rotary retained between the lateral walls 62, 63 of the central path 61 with its longitudinal axis being located perpendicularly to the central path longitudinal axis and having a three circular grooves 77a, 77b, 77c;

a first pulley 78, having a central elongated member axis including a first end and a second end which is joined to the center of the pulley, wherein the first end of the axis member is rotary retained to the inferior longitudinal wall 64 of the central path 61 in such way that it is positioned in a perpendicularly relationship with respect to the central path longitudinal axis;

a second pulley 79, having a central elongated member axis including a first end and a second end which is joined to the center of the pulley, wherein the first end of the axis member is rotary retained to the second longitudinal wall 64 of the central path 61 in such way that it is positioned in a perpendicularly relationship with respect to the central path longitudinal axis;

a third pulley 80, having a central elongated member axis including a first end and a second end which is joined to the center of the pulley, wherein the first end of the axis member is retained to both lateral walls 62, 63 of the central path 61 in such way that it is positioned between them;

wherein the first sluing drum 74, second sluing drum 76 and third pulley 80 are located along the central path 61 in said order in a zig-zag pattern and retained to both central path 61 lateral walls as described above;

wherein the first 78 and second 79 pulley are located along the central path 61 in said order in a zig-zag pattern and retained to the second central path 61 inferior longitudinal wall 64 as described above;

wherein the second cable 21b passing through the central path 61, passes by and surrounds the circular groove 75 of the first sluing drum 74 and passes by and surrounds the third pulley 78;

wherein the third cable 21c passes by and surrounds a third circular groove 77c of the second sluing drum 76, and passes by the second 78 and third 79 pulleys; and wherein the fifth 21e and sixth 21f cable passes by and surrounds a correspondent circular groove 77b, 77a of the second sluing drum 76;

a fifth connection element 14 including a first open end 81 and a second end 82 having a cylindrical shape, a circular cross section and a circular internal and external wall, an entrance opening, an exit opening, and a longitudinal and transversal axis, wherein the first end including a first rounded lateral wall 82, and a second rounded longitudinal wall 83 having a central circular recess 84, each depending from the second end circular wall and each including a central coincident pin hole (not shown), wherein the pin hole of the second rounded lateral wall is located at a central portion of the circular recess 85 and wherein the second end 82 includes cylindrical connection member 86 including an open transversal lateral housing 87 opened to the exterior of the rotary connection means 86 and a cylindrical linking member 86*a* having two circular passages 88*a*, 88*b*, and having:

a circular spring 89 tightly received inside the circular recess 85 located at the second rounded lateral wall 84;

a first sluing drum 90 having a first and a second end, each including an elongated longitudinal axis member 90*a*, wherein the ends of the longitudinal axis member passes through the pin hole of the first 83 and second 84 rounded lateral wall respectively, thus rotary and transversally retained between the first 83 and second 84 rounded longitudinal wall in a central portion thereof and including three circular grooves 91*a*, 91*b*, 91*c*, and wherein each end of the elongated member axis protrudes over the pinhole of the first rounded lateral wall 83 and over the pinhole of the second rounded lateral wall 84;

a second sluing drum 92 having a first and a second end, and a longitudinal axis, wherein said second sluing drum is rotary and transversally retained between the first 83 and second 84 rounded lateral wall and including one circular groove 93, wherein the second sluing drum 92 is located next to the first sluing drum 90 in a parallel relationship and off center with respect to the longitudinal axis;

a third 94 and a fourth 96 sluing drums, each having a first and a second end and a circular groove 95 (only the circular groove of the third sluing drum shown), and each parallely located with respect to each other and aligned with respect to the transversal axis;

a first 97 and a second 98 pulley, each having a central elongated member axis including a first end and a second end which is joined to the center of the pulley 97, 98, wherein the first end of the axis member of the first pulley 97 is attached to the interior circular wall of the cylindrical connection member 86 and the first end of the axis member of the second pulley 98 is attached to the interior circular wall of the cylindrical linking member 86*a* in such way that each axis is positioned in a perpendicularly relationship with respect to the longitudinal axis, and in a parallel relationship with respect to the transversal axis, wherein the first pulley 97 including only one circular groove 97*a* and the second pulley 98 including a first 98*a* and a second 98*b* circular groove and wherein the first pulley 97 is located next to the third 94 and fourth 96 parallel sluing drums and wherein the second pulley 98 is located next to the first pulley 97;

a third pulley 99 having a central elongated member axis including a first end and a second end which is joined to the center of the pulley, said third pulley rotary retained inside the open transversal lateral housing 87 wherein the first end of the axis member is retained to a wall of the open transversal lateral housing 87 in such way that it is positioned in a parallel relationship with respect to the longitudinal axis, and in a perpendicular relationship with respect to the transversal axis;

wherein a third cable 21*c* exiting the fourth connection element 12 enters the fifth connection element 14 through the first open end 81 and passes by and surrounds a correspondent groove 91*c* of the first sluing drum 90 and third sluing drum 94 and is guided through the cylindrical connection member 86 and cylindrical linking member 86*a* and exits the fifth connection element 14 through the first circular passage 88*a*;

wherein a fifth cable 21*e* exiting the fourth connection element 12 enters the fifth connection element 14 through the first open end 81 and passes by and surrounds the respective groove 91*b* of the first sluing drum 90 and second sluing drum 92 and is guided through the cylindrical connection member 86 inside of which it passes by the first pulley 97 and the first groove 98*a* of the second pulley 98 and through the cylindrical linking member and exits the fifth connection element 14 through the second circular passage 88*b*;

wherein the sixth cable 21*f* exiting the fourth connection element 12 enters the fifth connection element 14 through the first open end 81 and passes by and surrounds a respective groove 91*a* of the first 90 and fourth 96 sluing drum and is guided through the cylindrical connection member 86 inside of which it passes by the first pulley 97, through the cylindrical linking member 86*a* inside of which it passes by the second groove 98*b* of the second pulley 98, makes a turn of 90°, passes by the third pulley 99 and exits the fifth element 14 through the open transversal lateral housing 87;

wherein the second cable 21*b* exiting the fourth connection element 12 is linked to the first open end 81 second rounded lateral wall 84;

wherein the fifth connection element 14 is pivotally retained inside the second open end 59 of the fourth connection element 12 by locking the ends of the elongated longitudinal axis member 90*a* protruding over the first rounded lateral wall 83 and over the second rounded lateral wall 84 inside the first and second 70*a* pin holes located at a correspondent second open end 59 rounded lateral wall 69, 70 of the fourth connection element in such way that the whole first end 81 of the fifth connection element 14 is retained between the second open end 59 first 52 and second 53 lateral walls so that said fourth connection element 12 is able to move up to 90° upwards until reaching a horizontal position parallel to the Z axis and downwards until reaching a vertical position parallel to the Y axis, taking as reference the fourth connection element 12 resting position, when the second stepper motor pulls the second cable 21*b* linked to the first open end 81 second rounded lateral wall 84 and wherein the resting position for the fifth connection element comprises the position parallel to the Y axis; and wherein the circular spring 89 remains tightly retained between an internal face of the second end 59 second rounded lateral wall 70 of the fourth connection element 12 and the circular recess 85 of the fifth connection element 14 second rounded lateral wall 84 thus applying a torsional force over said two elements, forcing the fifth connecting element 14 to return to its resting position;

a sixth connection element 16 including a longitudinal and transversal axis, a first open end 100 having a cylindrical shape and a circular cross section including a hollow rotary connection section (not shown) having a circular internal wall, rotary receiving and linking the cylindrical linking member 86*a* of the fifth connection element 14 thus rotary linking the fifth 14 and sixth 16 connection element, and a second open end 101 having a first rounded lateral wall 102, a second rounded lateral wall 103 each including a central coincident pin hole 103*a*, 103*b* and an "inferior" longitudinal wall 104 each depending from the first open end 100, and having:

a first pulley 105 having a central elongated member axis including a first end and a second end which is rotary joined to the center of the pulley, wherein the first end of the axis member is retained to the "inferior" longitudinal wall 104 in such way that its central elongated member axis is located perpendicularly to the longitudinal wall 104 and between both lateral walls 102, 103;

a second pulley 106 having a central elongated member axis including a first end and a second end which is rotary joined to the center of the pulley, wherein the first end of the axis member is retained to the "inferior" longitudinal wall 104, next to the first pulley 105, in such way that its central elongated member axis is located perpendicularly to the longitudinal wall 104 and between both lateral walls 102, 103;

a sluing drum 107 having a first and a second end, and a longitudinal axis, wherein said sluing drum is rotary and transversally retained between the lateral walls 102, 103, with its longitudinal axis being located perpendicularly to the sixth connection 16 element longitudinal axis and "over" both pulleys 105, 106 and having one circular groove 108;

wherein the sixth cable 21f which exits the fifth connection element 14 by open transversal lateral housing 87 of the Cylindrical connection member 86 which is received and rotary retained inside the hollow rotary connection section of the sixth connection element 16, is linked to the circular internal wall of the sixth connection element 16 rotary connection section, thus connecting the sixth connection element 16 directly to a sixth stepper motor, so that when the stepper motor pulls the sixth cable 21f, it laterally pulls the sixth connection element 16 thus rotating it over the rotary connection which connects it to the fifth connection element 14;

wherein the fifth cable 21e exiting the fifth connection element 14 enters the sixth connection element 16 through the first open end 100, passes by and surrounds the first pulley 105, passes by the second pulley 106 thereafter and exits the sixth connection element 16 by the second open end 101;

wherein the third cable 21c exiting the fifth connection element 14 enters the sixth connection element 16 through the first open end 100 passes by the sluing drum 107 and exits the sixth connection element 16 by the second open end 101; and wherein the sixth connection element 16 is able to rotate over its own axis over the rotary connection as previously described, and is able to move up to 90° upwards until reaching a horizontal position parallel to the Z axis and downwards until reaching a vertical position parallel to the Y axis together with the fifth connection element 14;

a gripping tool 18 comprising:

a hollow main body 109 having a rectangular shape, including a first end 110 having a semi-cylindrical wall having a circular passage groove 111, an elongated cable receiving section 112 including a passage (not shown) to the interior of the hollow main body 109 located next to the circular passage groove 111, a first 113 and a second (not shown) longitudinal wall, a first 114 and a second 115 lateral walls, a hollow interior a second open end 116, and a cable attaching element located (not shown) inside the hollow interior of the hollow main body 109 at a central portion thereof, wherein the first end of the hollow main body 109, having a central superior circular recess 117 at the first lateral wall 114, wherein the first end of the hollow main body 109 having a coincident pin hole (not shown) at each lateral wall 114, 115, wherein the pin hole of the first lateral wall 114 is located at a central portion of the circular recess 117, and wherein the first 113 and second longitudinal walls each including a coincident perforation at a central portion thereof, and further having;

a circular spring 119 tightly received inside the circular recess 117 located at the first rounded lateral wall 114;

a fixed plier 120, joined and depending from the second lateral wall, first longitudinal wall 113 and second longitudinal wall 114; P2 a pulley 121, having a central elongated member axis including a first end and a second end which is joined to the center of the pulley, each one rotary retained inside the gripping tool hollow main body 18 wherein the first and second end passes through a respective perforation 103a, 103b of a respective lateral wall 114, 115 and each one protruding over its respective lateral wall 114, 115, thus rotary joining the pulley 121 to the first and second lateral walls 114, 115, so that its elongated member axis is located parallel to both longitudinal walls 113 and perpendicularly to the lateral walls 113, 114 and wherein it is positioned in such way that the pulley 121 is concentric with the first end 110 semi-cylindrical wall cross section and coinciding with the circular passage groove 111;

a pivotal second plier 122, having a first 123 and a second end 124, wherein the first end 123 has a drum 125 including a first and a second end having a respective pin 126 (only the pin of the first end shown), a circular groove 127 near the second end and a longitudinal axis, wherein the drum is pivotally joined inside the hollow main body at a central portion thereof so that the pins of both ends 126 are pivotally retained inside a respective pin hole 118 of a respective longitudinal wall 113, and thus pivotally linking the pivotal plier 122 and forming a complete and symmetrical pair of pliers 120, 122 with the fixed plier 120;

wherein the gripping tool hollow main body 109 first end 110 is pivotally retained inside the second open end 101 of the sixth connection element 16 by locking the ends of the first and second end of the pulley 121 central elongated member axis protruding over the first 114 and second 115 lateral walls inside the first 103a and second 103b coincident pin holes located at a correspondent second open end 101 rounded longitudinal wall 102, 103 of the sixth connection element 16 in such way that the whole first end 110 of the gripping tool hollow main body 109 is retained between the first 113 and second 114 longitudinal walls in such way that said gripping tool hollow main body 109 is able to move up to 90° upwards until reaching a horizontal position parallel to the Z axis and downwards until reaching a vertical position parallel to the Y axis, taking as reference the fifth connection element 14 resting position, and wherein the resting position for the gripping tool 18 comprises the position parallel to the Y axis;

wherein the circular spring 119 remains tightly retained between an internal face of the first lateral wall 102 of the sixth connection element 16 and the circular recess 117 of the first lateral wall 114 of the griping tool 18 hollow main body 109 thus applying a torsional force over said two elements, forcing the griping tool 18 hollow main body to return to its resting position;

wherein the third cable 21c exiting the sixth connection element 16 is received inside the elongated cable receiving section 112 and enters the gripping tool 18 hollow main body 109 in order to be linked to the cable attaching element, thus connecting the gripping element 18 hollow main body 109 directly to a third stepper motor, so that when the third stepper motor pulls the third cable 21c, it pulls the gripping tool causing it to move up to 90° upwards until reaching a horizontal position parallel to the Z axis;

wherein it is further included a circular spring 128 tightly retained around the drum 125 near its first end and between both gripping tool 18 hollow main body 109 lateral walls 114, 115, thus forcing the pliers to open, which comprise its resting position;

wherein the fifth cable 21e exiting the sixth connection element 16 enters the gripping tool 18 hollow main body 109 by the circular passage groove 111, passes by the pulley 121 and is wound around the drum 125 of the pivotal plier 122, thus directly connecting the fifth stepper motor to the pivotal plier 122, so that when the fifth stepper motor pulls the fifth cable 21e it causes the drum of the pivotal plier 122 to rotate, thus pivoting the pivotal plier 122 and opening the pliers, wherein the resting position for the pliers is at a closed position.

A camera may be included in the second end of the support means hollow cylinder, thus allowing the surgeon to have an impeded view of both robotic arms inside the patient's body from a central rear perspective.

Although it was described that the means for driving each element comprises a system of cables and stepper motors, said means may be comprised by any other known means, such as a transmission system comprised by a plurality of gears.

Also, the invention is not limited to the above referred number of movable elements, since it may be comprised by a further number of movable elements thus increasing the flexibility and movement combinations the device is capable to achieve.

Each one of the stepper motors are connected to control means comprising a computer including a control interface for the surgeon such a pair of joysticks, control gloves or an upper limb exoskeleton for a more realistic control of both arms.

Figure 27:
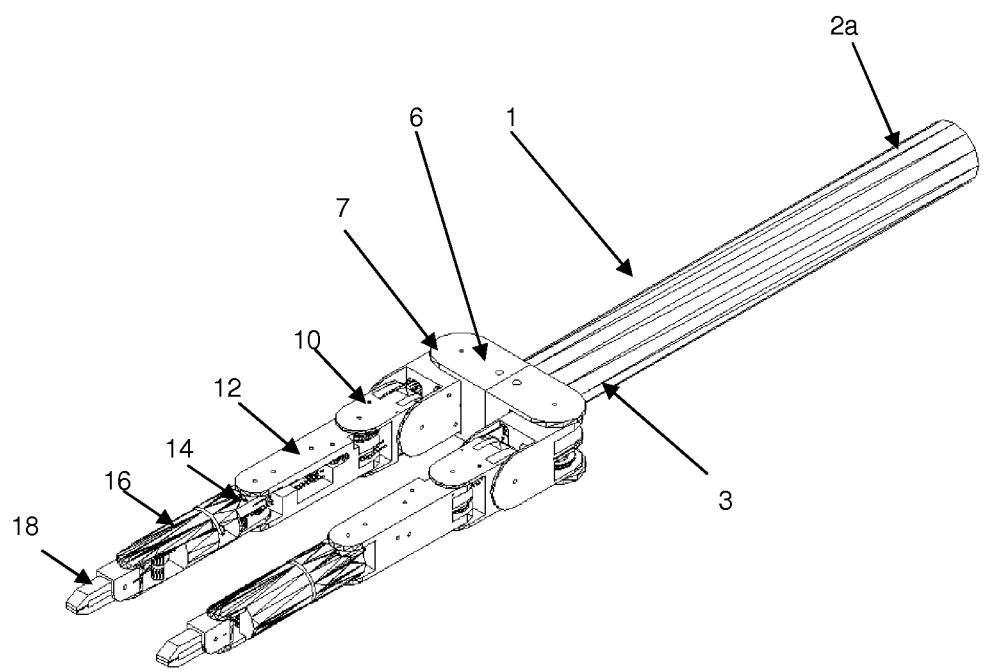
FIG. 27 is a perspective view of the robotical surgical device of the present invention including both robotic arms in an extended position ready for entering to a patient's body through a surgical incision.

For performing a minimal invasive surgery using the device of the present invention, it is necessary to practice only one incision the enters the patient's body through an incision by parallely extending both arms, thus reducing the diameter necessary for both arms to enter through the incision as shown in FIG. 27.

Furthermore, in combination with the robotic surgical device of the present invention, it is also provided a method for performing a minimal invasive surgery in a patient using the device of the present invention, wherein said method comprising the steps of:

making one incision in patient's body and preparing patient for a laparoscopic operation;

introducing through said incision a robotic surgical device comprising two or more robotic arms each having: at least six connection elements including manipulating means; at least six joints; driving means connected to each connection element and to the manipulating means for moving each of the connection elements and the manipulating means and remote control means for each robotic arm; wherein each of the arms have at least fourteen degrees of movement; and operating each robotic arm using the remote control means.

Finally it must be understood that the robotic surgical device of the present invention, is not limited exclusively to the embodiments above described and illustrated and that the persons having ordinary skill in the art can, with the teaching provided by the invention, to make modifications to the robotic surgical device of the present invention, which will clearly be within of the true inventive concept and of the scope of the invention which is claimed in the following claims.

What is claimed is:

1. A robotic surgical device comprising:

support means comprising an elongated hollow cylinder having a first and a second end and having a diameter size adequate for entering through a standard sized laparoscopic surgical opening;

a first and a second robotic arm each positioned in a parallel relationship from each other;

driving means for driving both robotic arms, comprising: a first and a second group of seven stepper motors, each group attached to a base and driving a correspondent robotic arm, wherein the motors of each group are aligned in two parallel rows and wherein each motor drives a rotary pulley located at a superior portion thereof;

movement transmission means for each stepper motor, each comprising a cable attached to the pulley of a respective motor for a total of fourteen cables divided in two groups of seven cables, each group corresponding to a robotic arm, wherein each of the cables attached to its respective pulley, passes by a correspondent series of circular grooves, each located at subsequent pulleys, thus lineally guiding each cable along subsequent pulleys so that a first pulley has one circular groove, the second pulley has two circular grooves, one for its own cable and one for the passing cable of the previous pulley and so on, thus avoiding the entanglement of the cables, and wherein each cable is pulled when the pulley rotates in one direction and is loosened when the pulley rotates in an opposite direction, and wherein both groups of cables are aligned and conducted through the elongated cylinder entering a first end and exiting through a second end thereof;

wherein each robotic arm comprises:

a first connection element fixedly attached to the support means having a longitudinal axis, a first open end and a second open end, and pivoting linking means, wherein in the resting position, the longitudinal axis of the first connection element, is located at a position parallel to the X axis;

a second connection element having a longitudinal axis, a first open end and a second open end, pivotally linked to the pivoting linking means of the first connection element, said second connection element able to pivot up to 90° to the front until the longitudinal axis or the second connection element reaches a position parallel to the Z axis and to a side until its longitudinal axis reaches a position parallel to the X axis, taking as reference the first connection element resting position, having pivoting linking means allowing a forward and backward pivoting movement and wherein in the resting position, the longitudinal axis of the second connection element is located at a position parallel to the X axis;

a third connection element having a longitudinal axis, a first open end and a second open end, pivotally linked to the pivoting linking means of the second connection element, said third connection element able to pivot up to 90° upwards until its longitudinal axis reaches a horizontal position parallel to the X axis and downwards until its longitudinal axis reaches a vertical position parallel to the Y axis, taking as reference the second connection element resting position, having pivoting linking means allowing an upward and downward pivoting movement, and wherein in the resting position, the longitudinal axis of the third connection element is located at a position parallel to the Y axis;

a fourth connection element having a longitudinal axis, a first open end and a second open end, pivotally linked to the pivoting linking means of the third connection element, said fourth connection element able to pivot up to 90° upwards until the longitudinal axis of the fourth connection element reaches a horizontal position parallel to the Z axis and downwards until its longitudinal axis reaches a vertical position parallel to the Y axis, taking as reference the third connection element resting position, having pivoting linking means allowing an upward and downward pivoting movement, and wherein in the resting position, the longitudinal axis of the fourth connection element is located at a position parallel to the Y axis;

a fifth connection element having a longitudinal axis, a first open end a second end having rotary linking means allowing concentric rotation over a single axis, pivotally linked to the pivoting linking means of the fourth connection element, said fifth connection element able to pivot up to 90° upwards until the longitudinal axis of the fifth connection element reaches a horizontal position parallel to the Z axis and downwards until its longitudinal axis reaches a vertical position parallel to the Y axis, taking as reference the fourth connection element resting position, and wherein in the resting position, the longitudinal axis of the fifth connection element is located at a position parallel to the Y axis;

a sixth connection element having a longitudinal axis, a first open end rotary linked to the rotating linking means of the fifth connection element and a second open end having pivoting linking means allowing the sixth connection to move up to 90° upwards until the longitudinal axis of the sixth connection element reaches a horizontal position parallel to the Z axis and downwards until its longitudinal axis reaches a vertical position parallel to the Y axis together with the fifth connection element, said sixth connection element able to rotate 360° over the connection element's own longitudinal axis, and wherein in the resting position, the longitudinal axis of the sixth connection element is located at a position parallel to the Y axis;

a gripping tool, pivotally linked to the pivoting linking means of the sixth connection element and having a longitudinal axis, said gripping tool able to pivot up to 90° upwards until the longitudinal axis of the sixth connection element reaches a horizontal position parallel to the Z axis and downwards until its longitudinal axis reaches a vertical position parallel to the Y axis, taking as reference the sixth connection element resting position, and wherein in the resting position, the longitudinal axis of the gripping tool is located at a position parallel to the Y axis; and wherein the robotic surgical device including driving means comprising a first and a second group of seven stepper motors, each group attached to a base and driving a correspondent robotic arm, wherein the motors of each group are aligned in two parallel rows and wherein each motor drives a rotary pulley located at a superior portion thereof;

wherein each connection element is connected to a correspondent stepper motor by means of a cable attached to the pulley of a respective motor for a total of fourteen cables divided in two groups of seven cables, each group corresponding to a robotic arm wherein each of the cables attached to its respective pulley, passes by a correspondent series of circular grooves, each located at subsequent pulleys, thus lineally guiding each cable along subsequent pulleys, thus avoiding the entanglement of the cables, and wherein each cable is pulled when the pulley of a respective stepper motor rotates in one direction and is loosen when the pulley rotates in an opposed direction, and wherein both groups of cables are aligned and conducted through the support means;

wherein a first corresponding group of seven cables enter the first connection element through the first open end and wherein a first, second, third, fourth, fifth, sixth, and seventh cable of said first corresponding group, exit the first connection element through the second open end;

wherein a first, second, third, fourth, fifth, sixth, and seventh cable exiting the first connection element, enters the second connection element through the first open end and wherein a first, second, third, fifth, sixth, and seventh cable exit the second connection element through the second open end;

wherein a first, second, third, fifth, sixth, and seventh cable exiting the second connection element enters the third connection element through its first open end and wherein the first, second, third, fifth and sixth cable exit the third connection element through the second open end; wherein a first, second, third, fifth and sixth cable exiting the third connection element enters the fourth connection element through its first open end and wherein a second, third, fifth and sixth cable exit the fourth connection element through the second open end;

wherein a second, third, fifth and sixth cable exiting the fourth connection element enters the fifth connection element through its first open end and wherein a third, fifth and sixth cable exit the fourth connection element through the fourth connection element's second open end;

wherein a third, fifth and sixth cable exit the fifth connection element through its second end enters the sixth connection element through its first open end and wherein a third and fifth cable exit the sixth connection element through the sixth connection element's second open end; and wherein a third and fifth cable exiting the sixth connection element through its second open end enters the gripping tool through its second open end, wherein the first connection element comprises: a first connection element comprising a hollow quadrangular member having a first and a second longitudinal wall, a central longitudinal axis, a first end and a second open rounded end, including a first and a second pin holes located at each longitudinal wall near the first end of the first connection element, a rectangular aperture at a lateral side near the first end, said first connection element been fixedly attached to the second end of the hollow elongated cylinder in such way that its longitudinal axis is located perpendicularly to the hollow cylindrical tube and the lateral rectangular aperture coincide with the second end of the hollow cylindrical tube and having:

a rotating sluing drum including a pin at each end, each pin rotary received inside the pin holes so that the ends of the first rotary sluing drum are rotary linked to both longitudinal walls and located between them inside the first connection element near its first end and aligned with its central longitudinal axis, having seven concentric circular grooves;

a first and a second opposed pin holes each located at a correspondent longitudinal wall near the second end of the first connection element, each aligned with the central longitudinal axis; and wherein the first corresponding group of cables enter the first connection element through the rectangular aperture, each passing by the sluing drum and guided by a respective concentric circular groove and exiting the first connection element through the second open end.

2. The robotic surgical device as claimed in claim 1, wherein the second connection element includes:

a first open end and a second open end, and a central portion including a first and a second passage, wherein the first end including a superior rounded longitudinal wall having a central superior circular recess, a central rounded longitudinal wall, and an inferior rounded longitudinal wall, each depending from the central portion and each including a central coincident pin hole, wherein the pin hole of the superior rounded longitudinal wall is located at a central portion of the circular recess and wherein the second open end includes a first rounded lateral wall and a second opposed rounded lateral wall each extending from the central portion and each respectively having a first and a second pin hole at a central portion thereof, said second connection element further having:

six pulleys having a central perforation, each one located below the other forming a vertical row, and wherein a first, second and third pulley are located and rotary retained between the superior rounded longitudinal wall and the central rounded longitudinal wall, and a fourth, fifth and sixth pulley are located and rotary retained between the central rounded longitudinal wall and the inferior rounded longitudinal wall;

a pin passing through the pin hole of the superior rounded longitudinal wall, through the central perforation of the first, second and third pulley, through the pin hole of the central rounded longitudinal wall, through the central perforation of the fourth, fifth and sixth pulley and through the pinhole of the inferior rounded longitudinal wall, thus rotary retaining the six pulleys and wherein the pin protrudes over the pinhole of the superior rounded longitudinal wall and below the inferior rounded longitudinal wall;

a circular spring tightly received inside the circular recess located at the superior rounded longitudinal wall;

wherein a first, second and third cable exiting the first connection element each enters the second connection element through the first open end and passes by and surrounds a correspondent first, second and third pulley and are guided through the first passage of its central portion to the second open end through which they exist the second connection open end through which they exit the second connection element and wherein a fifth, sixth, and seventh cable exiting the first connection element, enters the second connection element through the first open end and passes by and surrounds a correspondent fourth, fifth and sixth pulley and are a guided through the second passage of its central portion to the second open end through which they exit the second connection element;

wherein a fourth cable is linked to the central portion of the second connection element, thus connecting the second connection element directly to a fourth stepper motor, thus driving the second connection element;

wherein the second connection element is pivotally retained inside the second open rounded end of the first connection element in such way that the whole first end of the second connection element including the superior, central and inferior rounded longitudinal walls and pulleys are retained inside the second open rounded end of the first connection element so that said second connection element is able to pivot up to 90° to the front until its longitudinal axis reaches a position parallel to the Z axis and to a side until its longitudinal axis reaches a position parallel to the X axis, taking as reference the first connection element resting position, when a fourth stepper motor pulls the fourth cable linked to the second connection element and wherein in the resting position, the longitudinal axis of the second connection element is located at a position parallel to the X axis;

wherein the circular spring remains tightly retained between the first connection element and the circular recess of the superior rounded longitudinal wall of the second connecting element thus applying a torsional force over said two elements, forcing the second connecting element to return to its resting position; and further including a first and a second lateral pulley each respectively linked at a superior and inferior portion of the first and second rounded lateral wall between them and inside the second open end of the second connection element, and wherein the seventh cable passing through the second passage passes by said first and second lateral pulley before emerging from the second connection element by the second open end.

3. The robotic surgical device as claimed in claim 1, wherein the third connection element including:

a first open end and a second open end, and a central portion including a first and a second passage wherein the first end including a first rounded longitudinal wall having a central superior circular recess, a central rounded longitudinal wall, and an third rounded longitudinal wall, each depending from the central portion and each including a central coincident pin hole, wherein the pin hole of the first rounded longitudinal wall is located at a central portion of the circular recess and wherein the second open end includes a first rounded lateral wall and a second rounded lateral wall each extending from the central portion and including a correspondent first and a second pin holes, and having:

five pulleys having a central perforation, each one located below the other forming a linear row, and wherein a first and second pulley are located and rotary retained between the first rounded longitudinal wall and the central rounded longitudinal wall, and a third, fourth and fifth pulley are located and rotary retained between the central rounded longitudinal wall and the third rounded longitudinal wall;

a pin passing through the pin hole of the first rounded longitudinal wall, through the central perforation of the first and second pulley, through the pin hole of the central rounded longitudinal wall, through the central perforation of the third, fourth and fifth pulley and through the pinhole of the third rounded longitudinal wall in that order, thus rotary retaining the five pulleys and wherein the pin protrudes over the pinhole of the first rounded longitudinal wall and below the third rounded longitudinal wall;

a circular spring tightly received inside the circular recess located at the first rounded longitudinal wall;

wherein a fifth, and a sixth cable exiting the second connection element each enters the third connection element through the first open end and passes by and surrounds a correspondent second, and first pulley and are guided through the first passage of its central portion to the second open end through which they exit the third connection element and wherein a first, second and third cable exiting the second connection element, enters the third connection element through the first open end and passes by and surrounds a correspondent fifth, fourth and third pulley and are guided through the second passage of its central portion to the second open end through which they exit the third connection element;

wherein a seventh cable is linked to the central portion of the third connection element, thus connecting the third connection element directly to a seventh stepper motor, thus driving the third connection element;

wherein the third connection element is pivotally retained inside the second open end of the second connection element in such way that the whole first end of the third connection element including the first, central and third rounded longitudinal walls and pulleys are retained inside the second open end of the second connection element in such way that said third connection element is able to move up to 90° upwards until its longitudinal axis reaches a horizontal position parallel to the X axis and downwards until its longitudinal axis reaches a vertical position parallel to the Y axis, taking as reference the second connection element resting position, when a seventh stepper motor pulls the seventh cable linked to the third connection element and wherein in the resting position, the longitudinal axis of the third connection element is located at a position parallel to the Y axis; and wherein the circular spring remains tightly retained between the second connection element and the circular recess of the first rounded longitudinal wall of the third connecting element thus applying a torsional force over said two elements, forcing the third connecting element to return to its resting position.

4. The robotic surgical device as claimed in claim 1, wherein the fourth connection element including:

a first open end and a second open end, and an elongated central portion including a first and a second passage and a central path having a longitudinal axis defined by a first and a second lateral wall and by an inferior longitudinal wall, wherein the first end including a first rounded lateral wall having a central superior circular recess, a central rounded lateral wall, and an third rounded lateral wall, each depending from the central portion and each including a central coincident pin hole, wherein the pin hole of the superior rounded longitudinal wall is located at a central portion of the circular recess and wherein the second open end includes a first rounded lateral wall and a second rounded lateral wall extending from the central portion each having a central pin hole, and having:

four pulleys having a central perforation, each one located below the other forming a linear row, and wherein a first and a second pulley are located and rotary retained between the first end first rounded lateral wall and the first end central rounded longitudinal wall, and a third and fourth pulley are located and rotary retained between the first end central rounded longitudinal wall and the first end third rounded longitudinal wall;

a pin passing through the pin hole of the first end first rounded longitudinal wall, through the central perforation of the first and second pulley, through the pin hole of the first end central rounded longitudinal wall, through the central perforation of the third and fourth pulley and through the pinhole of the first end third rounded longitudinal wall in that order, thus rotary retaining the four pulleys and wherein the pin protrudes over the first end first rounded longitudinal wall and below the first end third rounded longitudinal wall;

a circular spring tightly received inside the circular recess located at the first end first rounded longitudinal wall;

wherein a sixth and fifth cable exiting the third connection element each enters the fourth connection element through the first open end and passes by and surrounds a correspondent first and second pulley and are guided through the first passage of the central portion across the central path to the second open end through which they exit the fourth connection element and wherein a second and third cable exiting the third connection element, enters the fourth connection element through the first open end and passes by and surrounds a correspondent fourth and third pulley and are guided through the first passage of the central portion across the central path to the second open end through which they exit the fourth connection element;

wherein a first cable is linked to the first end third rounded lateral wall of the fourth connection element, thus connecting the fourth connection element directly to the first stepper motor, thus driving the fourth connection element;

wherein the fourth connection element is pivotally retained inside the second open end of the third connection element in such way that the whole first end of the fourth connection element including the first, central and third rounded longitudinal walls and pulleys are retained inside the second open end of the third connection element in such way that said fourth connection element is able to move up to 90° upwards until its longitudinal axis reaches a horizontal position parallel to the Z axis and downwards until its longitudinal axis reaches a vertical position parallel to the Y axis, taking as reference the third connection element resting position, when a first stepper motor pulls the first cable linked to the fourth connection element and wherein in the resting position, the longitudinal axis of the fourth connection element is located at a position parallel to the Y axis;

wherein the circular spring remains tightly retained between the third connection element and the circular recess of the first end first rounded lateral wall of the fourth connecting element thus applying a torsional force over said two elements, forcing the fourth connecting element to return to its resting position; and further including:

a first sluing drum having a first and a second end, and a longitudinal axis, wherein said first sluing drum is rotary and transversally retained inside the central path in such way that both ends are rotary retained between the lateral walls of the central path with its longitudinal axis being located perpendicularly to the central path longitudinal axis and having one circular groove;

a second sluing drum having a first and a second end, and a longitudinal axis, wherein said second sluing drum is rotary and transversally retained inside the central path in such way that both ends are rotary retained between the lateral walls of the central path with its longitudinal axis being located perpendicularly to the central path longitudinal axis and having a three circular grooves;

a first pulley, having a central elongated member axis including a first end and a second end which is joined to the center of the pulley, wherein the first end of the axis member is rotary retained to the inferior longitudinal wall of the central path in such way that it is positioned in a perpendicularly relationship with respect to the central path longitudinal axis;

a second pulley, having a central elongated member axis including a first end and a second end which is joined to the center of the pulley, wherein the first end of the axis member is rotary retained to the second longitudinal wall of the central path in such way that it is positioned in a perpendicularly relationship with respect to the central path longitudinal axis;

a third pulley, having a central elongated member axis including a first end and a second end which is joined to the center of the pulley, wherein the first end of the axis member is retained to both lateral walls of the central path in such way that it is positioned between them;

wherein the first sluing drum, second sluing drum and third pulley are located along the central path in said order in a zig-zag pattern and retained to both central path lateral walls as described above;

wherein the first and second pulley are located along the central path in said order in a zig-zag pattern and retained to the second central path inferior longitudinal wall as described above;

wherein the second cable passing through the central path, passes by and surrounds the circular groove of the first sluing drum and passes by and surrounds the third pulley;

wherein the third cable passes by and surrounds a third circular groove of the second sluing drum, and passes by the second and third pulleys; and wherein the fifth and sixth cable passes by and surrounds a correspondent circular groove of the second sluing drum.

5. The robotic surgical device as claimed in claim 1, wherein the fifth connection element including:

a first open end and a second end having a cylindrical shape, a circular cross section and a circular internal and external wall, an entrance opening, an exit opening, and a longitudinal and transversal axis, wherein the first end including a first rounded lateral wall, and a second rounded longitudinal wall having a central circular recess, each depending from the second end circular wall and each including a central coincident pin hole, wherein the pin hole of the second rounded lateral wall is located at a central portion of the circular recess and wherein the second end includes cylindrical connection member including an open transversal lateral housing opened to the exterior of the rotary connection means and a cylindrical linking member having two circular passages, and having:

a circular spring tightly received inside the circular recess located at the second rounded lateral wall;

a first sluing drum having a first and a second end, each including an elongated longitudinal axis, wherein the ends of the longitudinal axis member passes through the pin hole of the first and second rounded lateral wall respectively, thus rotary and transversally retained between the first and second rounded longitudinal wall in a central portion thereof and including three circular grooves, and wherein each end of the elongated member axis protrudes over the pinhole of the first rounded lateral wall and over the pinhole of the second rounded lateral wall;

a second sluing drum having a first and a second end, and a longitudinal axis, wherein said second sluing drum is rotary and transversally retained between the first and second rounded lateral wall and including one circular groove, wherein the second sluing drum is located next to the first sluing drum in a parallel relationship and off center with respect to the longitudinal axis;

a third and a fourth sluing drums, each having a first and a second end and a circular groove, and each parallely located with respect to each other and aligned with respect to the transversal axis;

a first and a second pulley, each having a central elongated member axis including a first end and a second end which is joined to the center of the pulley, wherein the first end of the axis member of the first pulley is attached to the interior circular wall of the cylindrical connection member and the first end of the axis member of the second pulley is attached to the interior circular wall of the cylindrical linking member in such way that each axis is positioned in a perpendicularly relationship with respect to the longitudinal axis, and in a parallel relationship with respect to the transversal axis, wherein the first pulley including only one circular groove and the second pulley including a first and a second circular groove and wherein the first pulley is located next to the third and fourth parallel sluing drums and wherein the second pulley is located next to the first pulley;

a third pulley having a central elongated member axis including a first end and a second end which is joined to the center of the pulley, said third pulley rotary retained inside the open transversal lateral housing wherein the first end of the axis member is retained to a wall of the open transversal lateral housing in such way that it is positioned in a parallel relationship with respect to the longitudinal axis, and in a perpendicular relationship with respect to the transversal axis;

wherein a third cable exiting the fourth connection element enters the fifth connection element through the first open end and passes by and surrounds a correspondent groove of the first sluing drum and third sluing drum and is guided through the cylindrical connection member and cylindrical linking member and exits the fifth connection element through the first circular passage;

wherein a fifth cable exiting the fourth connection element enters the fifth connection element through the first open end and passes by and surrounds the respective groove of the first sluing drum and second sluing drum and is guided through the cylindrical connection member inside of which the fifth cable passes by the first pulley and the first groove of the second pulley and through the cylindrical linking member and exits the fifth connection element through the second circular passage;

wherein the sixth cable exiting the fourth connection element enters the fifth connection element through the first open end and passes by and surrounds a respective groove of the first and fourth sluing drum and is guided through the cylindrical connection member inside of which it passes by the first pulley, through the cylindrical linking member inside of which it passes by the second groove of the second pulley, makes a turn of 90°, passes by the third pulley and exits the fifth element through the open transversal lateral housing;

wherein the second cable exiting the fourth connection element is linked to the first open end second rounded lateral wall;

wherein the fifth connection element is pivotally retained inside the second open end of the fourth connection element in such way that the whole first end of the fifth connection element is retained inside the second open end of the fourth connection element so that said fourth connection element is able to move up to 90° upwards until its longitudinal axis reaches a horizontal position parallel to the Z axis and downwards until its longitudinal axis reaches a vertical position parallel to the Y axis, taking as reference the fourth connection element resting position, when a second stepper motor pulls the second cable linked to the first open end second rounded lateral wall and wherein in the resting position, the longitudinal axis of the fifth connection element is located at a position parallel to the Y axis; and wherein the circular spring remains tightly retained between the fourth connection element and the circular recess of the fifth connection element second rounded lateral wall thus applying a torsional force over said two elements, forcing the fifth connecting element to return to its resting position.

6. The robotic surgical device as claimed in claim 1, wherein the sixth connection element including:

a longitudinal and transversal axis, a first open end having a cylindrical shape and a circular cross section including a hollow rotary connection section having a circular internal wall, rotary linked to the rotary linking means of the fifth connection element thus rotary linking the fifth and sixth connection element, and a second open end having a first rounded lateral wall, a second rounded lateral wall each including a central coincident pin hole and an inferior longitudinal wall each depending from the first open end, and having:

a first pulley having a central elongated member axis including a first end and a second end which is rotary joined to the center of the pulley, wherein the first end of the axis member is retained to the inferior longitudinal wall in such way that its central elongated member axis is located perpendicularly to the longitudinal wall and between both lateral walls;

a second pulley having a central elongated member axis including a first end and a second end which is rotary joined to the center of the pulley, wherein the first end of the axis member is retained to the inferior longitudinal wall, next to the first pulley, in such way that its central elongated member axis is located perpendicularly to the longitudinal wall and between both lateral walls;

a sluing drum having a first and a second end, and a longitudinal axis, wherein said sluing drum is rotary and transversally retained between the lateral walls, with its longitudinal axis being located perpendicularly to the sixth connection element longitudinal axis and over both pulleys and having one circular groove;

wherein the sixth cable which exits the fifth connection element is linked to the circular internal wall of the sixth connection element rotary connection section, thus connecting the sixth connection element directly to a sixth stepper motor, so that when the stepper motor pulls the sixth cable, it laterally pulls the sixth connection element thus rotating it over the rotary connection which connects it to the fifth connection element;

wherein the fifth cable exiting the fifth connection element enters the sixth connection element through the first open end, passes by and surrounds the first pulley, passes by the second pulley thereafter and exits the sixth connection element by the second open end;

wherein the third cable exiting the fifth connection element enters the sixth connection element through the first open end passes by the sluing drum and exits the sixth connection element by the second open end; and wherein the sixth connection element is able to rotate 360° over its own longitudinal axis over the rotary connection, and is able to move up to 90° upwards until its longitudinal axis reaches a horizontal position parallel to the Z axis and downwards until the sixth connection elements longitudinal axis reaches a vertical position parallel to the Y axis together with the fifth connection element.

7. The robotic surgical device as claimed in 1, wherein the gripping tool comprises:

a hollow main body having a rectangular shape, including a first end having a semi-cylindrical wall having a circular passage groove, an elongated cable receiving section including a passage to the interior of the hollow main body located next to the circular passage groove, a first and a second longitudinal wall, a first and a second lateral walls, a hollow interior a second open end, and a cable attaching element located inside the hollow interior of the hollow main body at a central portion thereof, wherein the first end of the hollow main body, having a central superior circular recess at the first lateral wall, wherein the first end of the hollow main body having a coincident pin hole at each lateral wall, wherein the pin hole of the first lateral wall is located at a central portion of the circular recess, and wherein the first and second longitudinal walls each including a coincident perforation at a central portion thereof, and further having;

a circular spring tightly received inside the circular recess located at the first rounded lateral wall;

a fixed plier joined and depending from the second lateral wall, first longitudinal wall and second longitudinal wall;

a pulley, having a central elongated member axis including a first end and a second end which is joined to the center of the pulley, each one rotary retained inside the gripping tool hollow main body wherein the first and second end passes through a respective perforation, of a respective lateral wall and each one protruding over its respective lateral wall, thus rotary joining the pulley to the first and second lateral walls, so that its elongated member axis is located parallel to both longitudinal walls and perpendicularly to the lateral walls and wherein it is positioned in such way that the pulley is concentric with the first end semi-cylindrical wall cross section and coinciding with the circular passage groove;

a pivotal second plier, having a first and a second end, wherein the first end has a drum including a first and a second end having a respective pin, a circular groove near the second end and a longitudinal axis, wherein the drum is pivotally joined inside the hollow main body at a central portion thereof so that the pins of both ends are pivotally retained inside a respective pin hole of a respective longitudinal wall, and thus pivotally linking the pivotal plier and forming a complete and symmetrical pair of pliers with the fixed plier;

wherein the gripping tool hollow main body first end is pivotally retained inside the second open end of the sixth connection element in such way that the whole first end of the gripping tool hollow main body is retained inside the second open end of the sixth connection element so that said gripping tool hollow main body is able to move up to 90° upwards until its longitudinal axis reaches a horizontal position parallel to the Z axis and downwards until its longitudinal axis reaches a vertical position parallel to the Y axis, taking as reference the fifth connection element resting position, and wherein in the resting position, the longitudinal axis of the gripping tool is located at a position parallel to the Y axis;

wherein the circular spring remains tightly retained between the sixth connection element and the circular recess of the first lateral wall of the gripping tool hollow main body thus applying a torsional force over said two elements, forcing the gripping tool hollow main body to return to its resting position;

wherein the third cable exiting the sixth connection element is received inside the elongated cable receiving section and enters the gripping tool hollow main body in order to be linked to the cable attaching element, thus connecting the gripping element hollow main body directly to a third stepper motor, so that when the third stepper motor pulls the third cable, it pulls the gripping tool causing it to move up to 90° upwards until its longitudinal axis reaches a horizontal position parallel to the Z axis;

wherein it is further included a circular spring tightly retained around the drum near its first end and between both griping tool hollow main body lateral walls, thus forcing the pliers to open, which comprise its resting position;

wherein the fifth cable exiting the sixth connection element enters the griping tool hollow main body by the circular passage groove, passes by the pulley and is wound around the drum of the pivotal, thus directly connecting a fifth stepper motor to the pivotal plier, so that when the fifth stepper motor pulls the fifth cable it causes the drum of the pivotal plier to rotate, thus pivoting the pivotal plier and opening the pliers, wherein the resting position for the pliers is at a closed position.

* * * * *